(12) United States Patent
Shia et al.

(10) Patent No.: US 7,399,776 B2
(45) Date of Patent: Jul. 15, 2008

(54) POLYAMINE COMPOUNDS FOR TREATING CHEMOKINE RECEPTOR MEDIATED DISEASES

(75) Inventors: Kak-Shan Shia, Taipei (TW); Gholam Hossein Hakimelahi, Taipei (TW); Jia-Liang Zhu, Taipei (TW); Chi-Feng Yen, Taipei (TW); Ying-Huey Huang, Taipei (TW); Yibin Xiang, Acton, MA (US); Hua-Chien Chen, Taipei (TW); Ching-Cheng Wang, Changhua (TW)

(73) Assignee: Taigen Biotechnology, Taipei (TW)

( * ) Notice: Subject to any disclaimer, the term of this patent is extended or adjusted under 35 U.S.C. 154(b) by 490 days.

(21) Appl. No.: 10/814,058

(22) Filed: Mar. 30, 2004

(65) Prior Publication Data
US 2005/0043366 A1  Feb. 24, 2005

Related U.S. Application Data

(60) Provisional application No. 60/459,768, filed on Apr. 2, 2003, provisional application No. 60/539,763, filed on Jan. 28, 2004.

(51) Int. Cl.
*A61K 31/40* (2006.01)
*A61K 31/18* (2006.01)
*A61K 31/165* (2006.01)
*A61K 31/15* (2006.01)
*A61K 31/195* (2006.01)

(52) U.S. Cl. ............ 514/352; 514/426; 514/601; 514/617; 514/639; 514/561; 514/649

(58) Field of Classification Search .......... None
See application file for complete search history.

(56) References Cited

U.S. PATENT DOCUMENTS

| 5,252,317 | A | * | 10/1993 | Keana ............ 424/9.33 |
| 5,567,411 | A | * | 10/1996 | Keana et al. ......... 424/9.1 |
| 5,719,193 | A | | 2/1998 | Bowlin et al. |
| 5,910,513 | A | | 6/1999 | Galey ............ 514/649 |
| 2005/0165063 | A1 | | 7/2005 | Yamazaki et al. |

FOREIGN PATENT DOCUMENTS

| JP | 62129858 A | 6/1987 |
| JP | 64-66117 | 3/1989 |
| JP | 1-272568 | 10/1989 |
| JP | 2002-543126 | 12/2002 |
| JP | 3714948 | 9/2005 |
| WO | WO 97/00245 | 1/1997 |
| WO | WO 00/02870 | 1/2000 |
| WO | WO 00/56729 | 9/2000 |
| WO | WO 00/66112 | 11/2000 |
| WO | WO 02/22600 A2 | 3/2002 |
| WO | WO 02/055112 A2 | 7/2002 |
| WO | WO 02/083143 A1 | 10/2002 |

OTHER PUBLICATIONS

Wuntz, T.P. et al., J. Med. Chem., vol. 33, No. 6, pp. 1549-1553, 1990.
Mohamadou et al., "Synthesis and Characterisation of Zinc(II) Complexes of Tripodal $N_7$ Ligands Involving Pyridine and Amine or Amide Nitrogen Donors. Crystal Structure of a Zine (II) Complex", J. Chem. Soc., Dalton Trans., 3320-3328, 2001.
Rannard et al., "The Selective Reaction of Primary Amines with Carbonyl Imidazole Containing Compounds: Selective Amide and Carbamate Synthesis", Org. Lett., 2:2117-2120, 2000.
Xu et al., "Specific Sequestering Agents for the Actinides. 28. Synthesis and Initial evaluation of Multidentate 4-Crabamoyl-3-hydroxy-1-methyl-2(1H)-pyridinone Ligands for in Vivo Plutonium (IV) Chelation", J. Med. Chem. 38:2606-2614, 1995.
Yu et al., "Study on Antioxidative Succinimide Dispersants," *Chemical Abstracts Service*, [Online] XP002452292, Abstract.
Tecilla et al. "Acceleration o p-Nitrophenyl Ester Cleavage by Zn (II)-Organized Molecular Receptors," *Journal of Organic Chemistry*, vol. 62, pp. 7621-7628 (1997) XP002452260.
Deroche et al., "A seven-Coordinate Manganese (II) Complex Formed with a Single Tripodal Heptadentate Ligand as a New Superoxide Scavenger," *Journal of the American Chemical Society*, vol. 118, No. 19, pp. 4567-4573 (1996) XP002452261.

* cited by examiner

*Primary Examiner*—Raymond J Henley, III
(74) *Attorney, Agent, or Firm*—Occhiuti Rohlicek & Tsao LLP

(57) ABSTRACT

This invention relates to a method for treating inflammatory diseases or immune diseases, developmental or degenerative diseases, or tissue injuries. The method includes administering to a subject in need thereof an effective amount of one or more compounds of the following formula. Each variable in this formula is defined in the specification.

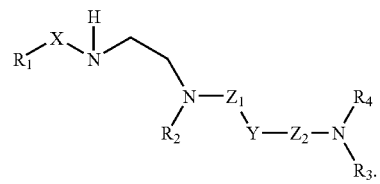

6 Claims, No Drawings

POLYAMINE COMPOUNDS FOR TREATING CHEMOKINE RECEPTOR MEDIATED DISEASES

CROSS REFERENCE TO RELATED APPLICATION

Pursuant to 35 USC § 119(e), this application claims priority to U.S. Provisional Application Ser. No. 60/459,768, filed Apr. 2, 2003, and U.S. Provisional Application Ser. No. 60/539,763, filed Jan. 28, 2004, the contents of which are incorporated herein by reference.

BACKGROUND

Chemokines are a family of cytokines that regulate the adhesion and transendothelial migration of leukocytes during an immune or inflammatory reaction (Mackay C. R., Nat. Immunol., (2001) 2:95; Olson et al., Am. J. Physiol. Regul. Integr. Comp. Physiol., (2002) 283:R7). Chemokines also regulate T cells and B cells trafficking and homing, and contribute to the development of lymphopoietic and hematopoietic systems (Ajuebor et al., Biochem. Pharmacol., (2002) 63:1191). Approximately 50 chemokines have been identified in humans. They can be classified into 4 subfamilies, i.e., CXC, CX3C, CC, and C chemokines, based on the positions of the conserved cysteine residues at the N-terminal (Onuffer et al., Trends Pharmacol Sci., (2002) 23:459). The biological functions of chemokines are mediated by their binding and activation of G protein-coupled receptors (GPCRs) on the cell surface. Take CXCR4 receptor for example, it can be activated by Stromal-derived factor-1 or SDF-1, a member of CXC chemokines.

SDF-1 was originally cloned from bone marrow stromal cell lines and found to act as a growth factor for progenitor B cells (Nishikawa et al., Eur. J. Immunol., (1988) 18:1767). SDF-1 also induces bone marrow colonization of hematopoietic precursor cells during embryogenesis (Bleul et al., J. Exp. Med., (1996) 184:1101). The physiological function of SDF-1 is mediated by CXCR4 receptor. Mice lacking SDF-1 or CXCR4 receptor show lethal abnormality in bone marrow myelopoiesis, B cell lymphopoiesis, and cerebellar development (Nagasawa et al., Nature, (1996) 382:635; Ma et al., Proc. Natl. Acad. Sci., (1998) 95:9448; Zou et al., Nature (1998) 393:595; Lu et al., Proc. Natl. Acad. Sci. (2002) 99:7090). CXCR4 receptor is expressed broadly in a variety of tissues, particularly in immune and central nervous systems, and has been described as the major co-receptor for HIV-1/2 on T lymphocytes. Although initial interest in CXCR4 antagonism focused on its potential application to AIDS treatment (Bleul et al., Nature (1996) 382:829), it is now becoming clear that CXCR4 receptor and SDF-1 are also involved in other pathological conditions such as rheumatoid arthritis, asthma, and tumor metastases (Buckley et al., J. Immunol., (2000) 165:3423). CXCR4 receptor and SDF-1 are also found widely expressed in many tissues during embryonic development. Further, the CXCR4/SDF-1 pathway has been shown to be critically involved in the regeneration of several tissue injury models. Specifically, it has been found that the SDF-1 level is elevated at an injured site and CXCR4-positive cells actively participate in the tissue regenerating process.

SUMMARY

This invention is based on the discovery that certain polyamine compounds are effective in treating inflammatory and immune diseases through their binding to chemokine receptors (e.g., CXCR3 or CXCR4 receptors).

In one aspect, this invention features polyamine compounds of the formula:

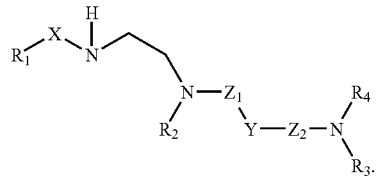

In the above formula, X is $-CH_2-$, $-C_2H_4-$, $-C_3H_6-$, $-CH_2-CH=CH-$, $-CH=CH-CH_2-$, $-C(O)-$, $-SO_2-$, or deleted; Y is aryl, heteroaryl, $C_3$-$C_8$ cycloalkyl, $C_5$-$C_8$ cycloalkenyl, $C_3$-$C_8$ heterocycloalkyl, or $C_5$-$C_8$ heterocycloalkenyl; each of $Z_1$ and $Z_2$, independently, is $-CH_2-$, $-C_2H_4-$, $-C_3H_6-$, $-CH=CH-$, $-CH=N-$, $-CH=N-NR-$, $-S-$, $-O-$, $-NR-$, $-C(O)-$, or $-SO_2-$; $R_1$ is H, $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl; $R_2$ is -$A_1$-$B_1$-$D_1$-$E_1$; $R_3$ is -$A_2$-$B_2$-$D_2$-$E_2$, deleted, or, together with $R_4$, is $C_4$-$C_{20}$ cycloalkyl, $C_4$-$C_{20}$ cycloalkenyl, $C_4$-$C_{20}$ heterocycloalkyl, or $C_4$-$C_{20}$ heterocycloalkenyl; provided that if $R_3$ is deleted, -$Z_2$-N— is —CH=N—; and $R_4$ is -$A_3$-$B_3$-$D_3$-$E_3$ or, together with $R_3$, is $C_4$-$C_{20}$ cycloalkyl, $C_4$-$C_{20}$ cycloalkenyl, $C_4$-$C_{20}$ heterocycloalkyl, or $C_4$-$C_{20}$ heterocycloalkenyl. Each of $A_1$, $A_2$, and $A_3$, independently, is $-CH_2-$, $-C_2H_4-$, $-C_3H_6-$, $-C_4H_8-$, $-C_5H_{10}-$, $-CH_2C(O)-$, $-C(O)CH_2-$, $-CH_2SO_2-$, $-SO_2CH_2-$, $-CH_2-CH=CH-$, $-CH=CH-CH_2-$, $-CH(CH_2OR)-$, $-CH(CH_2CH_2OR)-$, $-CH(COOR)-$, $-CH(CH_2COOR)-$, $-CH(C(O)NR_2)-$, or deleted. Each of $B_1$, $B_2$, and $B_3$, independently, is $-NR-$, $-CH_2-$, or deleted. Each of $D_1$, $D_2$, and $D_3$, independently, is $-CH_2-$, $-C_2H_4-$, $-C_3H_6-$, $-CH_2-CH=CH-$, $-CH=CH-CH_2-$, $-C(O)-$, $-SO_2-$, $-C(O)-NR-$, $-C(S)-NR-$, $-NR-C(O)-$, $-NR-C(S)-$, $-CH(OR)-$, $-CH(CH_2OR)-$, $-CH(CH_2CH_2OR)-$, $-CH(COOR)-$, 1,1-cyclopropylene, or deleted. Each of $E_1$, $E_2$, and $E_3$, independently, is H, $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl. Each R, independently, is H or $C_1$-$C_{10}$ alkyl.

Referring to the above formula, a subset of the just-described compounds are those in which X is $-CH_2-$ or $-CH(CH_3)-$, Y is phenyl or 4,4'-biphenyl, $Z_1$ is $-CH_2-$ or $-SO_2-$, $Z_2$ is $-CH_2-$ or $-SO_2-$, or $R_3$ is deleted.

The term "alkyl" refers to a saturated, linear or branched, non-aromatic hydrocarbon moiety, such as $CH_3$, $-CH_2-$, or branched $C_3H_7$. Referring to the above formula, $-C_2H_4-$ and $-C_3H_6-$ can be either linear or branched. The term "alkenyl" refers to a linear or branched, non-aromatic hydrocarbon moiety having at least one double bond, such as $-CH=CH_2$ or $-CH=CH-$. The term "alkynyl" refers to a linear or branched, non-aromatic hydrocarbon moiety having at least one triple bond, such as $-C\equiv CH$ or $-C\equiv C-$. The term "cycloalkyl" refers to a saturated non-aromatic cyclic hydrocarbon moiety. The term "cycloalkenyl" refers to a non-aromatic cyclic hydrocarbon moiety having at least one double bond in the ring. The term "heterocycloalkyl" refers to a saturated non-aromatic cyclic moiety having at least one ring heteroatom (e.g., O, N, and S). The term "heterocycloalkenyl" refers to a non-aromatic cyclic moiety having at least one ring heteroatom and at least one double bond in the ring. The term "aryl" refers to a hydrocarbon moiety having at least one aromatic ring. Examples of an aryl moiety include phenyl, phenylene, biphenyl, naphthyl, naphthylene, pyrenyl, anthryl, and phenanthryl. The term "heteroaryl" refers to a moiety having at least one aromatic ring which contains at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties. Examples of substituents for cycloalkyl, cycloalkenyl, heterocycloalkyl, heterocycloalkenyl, aryl, and heteroaryl include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfonyl, arylsulfonyl, heteroarylsulfonyl, $C_1$-$C_{10}$ alkylsulfonamide, arylsulfonamide, heteroarylsulfonamide, hydroxyl, halogen, mercapto, $C_1$-$C_{10}$ alkylmercapto, arylmercapto, cyano, nitro, acyl, acyloxy, carboxyl, amido, carbamoyl, and carboxylic ester. Examples of substituents for alkyl, alkenyl, and alkynyl include all of the above substitutents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl also include fused groups.

In another aspect, this invention features polyamine compounds of the same formula shown above. Referring to this formula, the same groups as those described above are assigned to each variable except that X is —$CH_2$—, —$C_2H_4$—, —$C_3H_6$—, —$CH_2$—CH=CH—, —CH=CH—$CH_2$—, —$SO_2$—, or deleted; Y is aryl, heteroaryl, $C_3$-$C_8$ cycloalkyl, $C_5$-$C_8$ cycloalkenyl, $C_3$-$C_8$ heterocycloalkyl, $C_5$-$C_8$ heterocycloalkenyl, or deleted; each of $D_1$, $D_2$, and $D_3$, independently, is —$CH_2$—, —$C_2H_4$—, —$C_3H_6$—, —$CH_2$—CH=CH—, —CH=CH—$CH_2$—, —$SO_2$—, —C(O)—NR—, —C(S)—NR—, —NR—C(O)—, —NR—C(S)—, —CH(OR)—, —CH($CH_2$OR)—, —CH($CH_2CH_2$OR)—, —CH(COOR)—, 1,1-cyclopropylene, or deleted; and $E_1$ is H, $C_1$-$C_{10}$ alkyl, $C_2$-$C_1$ alkenyl, $C_2$-$C_1$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, 5-membered heteroaryl, fused heteroaryl, substituted 6-membered heteroaryl, unsubstituted pryanyl, unsubstituted pyrazinyl, unsubstituted pyrimidinyl, or unsubstituted pyridazinyl.

Referring to the above formula, a subset of the just-described compounds are those in which X is —$CH_2$— or —CH($CH_3$)—, Y is deleted, $Z_1$ is —$CH_2$—, or $Z_2$ is —$CH_2$—.

In still another aspect, this invention features a method for treating an inflammatory or immune disease, a developmental or degenerative disease, or a tissue injury. The method includes administering to a subject in need thereof an effective amount of one or more compounds of the same formula shown above. Referring to this formula, X is —$CH_2$—, —$C_2H_4$—, —$C_3H_6$—, —$CH_2$—CH=CH—, —CH=CH—$CH_2$—, —C(O)—, —$SO_2$—, or deleted; Y is aryl, heteroaryl, $C_3$-$C_8$ cycloalkyl, $C_5$-$C_8$ cycloalkenyl, $C_3$-$C_8$ heterocycloalkyl, $C_5$-$C_8$ heterocycloalkenyl, or deleted; each of $Z_1$ and $Z_2$, independently, is —$CH_2$—, —$C_2H_4$—, —$C_3H_6$—, —CH=CH—, —CH=N—, —CH=N—NR—, —S—, —O—, —NR—, —C(O)—, or —$SO_2$—; $R_1$ is H, $C_1$-$C_{10}$ alkyl, $C_2$-$C_{10}$ alkenyl, $C_2$—$C_{10}$ alkynyl, $C_3$-$C_8$ cycloalkyl, $C_5$-$C_8$ cycloalkenyl, $C_3$-$C_8$ heterocycloalkyl; $C_5$-$C_8$ heterocycloalkenyl, aryl, or heteroaryl; $R_2$ is -$A_1$-$B_1$-$D_1$-$E_1$; $R_3$ is -$A_2$-$B_2$-$D_2$-$E_2$, deleted, or, together with $R_4$, is $C_{20}$ cycloalkyl, $C_4$-$C_{20}$ cycloalkenyl, $C_4$-$C_{20}$ heterocycloalkyl, or $C_4$-$C_{20}$ heterocycloalkenyl; provided that if $R_3$ is deleted, -$Z_2$-N— is —CH=N—; and $R_4$ is -$A_3$-$B_3$-$D_3$-$E_3$ or, together with $R_3$, is $C_4$-$C_{20}$ cycloalkyl, $C_4$-$C_{20}$ cycloalkenyl, $C_4$-$C_{20}$ heterocycloalkyl, or $C_4$-$C_{20}$ heterocycloalkenyl. Each of $A_1$, $A_2$, and $A_3$, independently, is —$CH_2$—, —$C_2H_4$—, —$C_3H_6$—, —$C_4H_8$—, —$C_5H_{10}$—, —$CH_2$C(O)—, —C(O)$CH_2$—, —$CH_2SO_2$—, —$SO_2CH_2$—, —$CH_2$—CH=CH—, —CH=CH—$CH_2$—, —CH($CH_2$OR)—, —CH($CH_2CH_2$OR)—, —CH(COOR)—, —CH($CH_2$COOR)—, —CH(C(O)$NR_2$)—, or deleted. Each of $B_1$, $B_2$, and $B_3$, independently, is —NR—, —$CH_2$—, or deleted. Each of $D_1$, $D_2$, and $D_3$, independently, is —$CH_2$—, —$C_2H_4$—, —$C_3H_6$—, —$CH_2$—CH=CH—, —CH=CH—$CH_2$—, —C(O)—, —$SO_2$—, —C(O)—NR—, —C(S)—NR—, —NR—C(O)—, —NR—C(S)—, —CH(OR)—, —CH($CH_2$OR)—, —CH($CH_2CH_2$OR)—, —CH(COOR)—, 1,1-cyclopropylene, or deleted. Each of $E_1$, $E_2$, and $E_3$, independently, is H, $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl. Each R, independently, is H or $C_1$-$C_{10}$ alkyl.

For example, one can administer to a subject having an above-described disease a compound of the above formula, in which X is —$CH_2$— or —CH($CH_3$)—, Y is phenyl, 4,4'-biphenyl, or deleted, $Z_1$ is —$CH_2$— or —$SO_2$—, $Z_2$ is —$CH_2$— or —$SO_2$—, or $R_3$ is deleted.

"Treatment" refers to administering one or more polyamine compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

An inflammatory disease is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis.

An immune disease is characterized by a hyper- or hypo-reaction of the immune system. Examples include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, graft rejection, including allograft rejection, and graft-versus-host disease), Sjogren's syndrome, human immunodeficiency virus infection, cancer (e.g., brain, breast, prostate, colon, kidney, ovary, thyroid, lung, and haematopoietic cancer), and tumor metastasis.

Developmental diseases are growth or differentiation related disorders that lead to loss-of-function or gain-of-function. Degenerative diseases generally refer to change of a tissue to a lower or less functional form. Examples of a developmental or degenerative disease include spinal muscular atrophy, Duchenne muscular dystrophy, Parkinson's disease, and Alzheimer's disease. Tissue injuries can be caused by oxidative stress (e.g., ischemia-reperfusion in stroke or myocardial infarction), complement activation, graft rejection, chemicals (e.g., alcohol-induced liver damage or mucosal tissue injuries in cancer therapy), viral infection (e.g., glomerular injuries associated with hepatitis C infection), and mechanical forces (e.g., sports injury). Examples of tissue injuries include brain injury, heart injury, liver damage, skeletal muscle injury, kidney damage, pancreatic injury, lung injury, skin injury, and gastrointestinal tract injury.

A subject in need of treatment of an above-described disease can also be concurrently administered with a polyamine compound described above and one or more other therapeutic agents. Examples of such a therapeutic agent include a steroidal or a non-steroidal anti-inflammatory drug, a COX2 inhibitor, a leukotriene receptor inhibitor, a prostaglandin modulator, a TNF modulator, and an immunosuppressive agent (e.g., cyclosporine A). The term "concurrently administered" refers to administering a polyamine compound and one or more other therapeutic agents at the same time or at different times during the period of treatment.

In a further aspect, this invention features a method for enhancing migration of bone marrow-derived cells to blood. The method includes administering to a subject in need thereof an effective amount of one or more compounds of the same formula shown above. Referring to this formula, the same groups as those described above are assigned to each variable. The term "bone marrow-derived cells" refers to cells originating from bone marrow. Examples of bone marrow-derived cells include, but are not limited to, CD34+ cells and CD133+ cells.

Also within the scope of this invention is a pharmaceutical composition that contains an effective amount of at least one of the above-mentioned polyamine compounds and a pharmaceutically acceptable carrier.

The polyamine compounds described above include the compounds themselves, as well as their salts, prodrugs, and solvates, if applicable. A salt, for example, can be formed between an anion and a positively charged group (e.g., amino) on a polyamine compound. Suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a polyamine compound. Suitable cations include sodium ion, potassium ion, magnesium ion, calcium ion, and an ammonium cation such as tetramethylammonium ion. The polyamine compounds also include those salts containing quaternary nitrogen atoms. Examples of prodrugs include esters and other pharmaceutically acceptable derivatives, which, upon administration to a subject, are capable of providing active polyamine compounds. A solvate refers to a complex formed between an active polyamine compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the polyamine compounds described above for use in treating an above-described disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are exemplary compounds, compounds 1-126, of this invention:

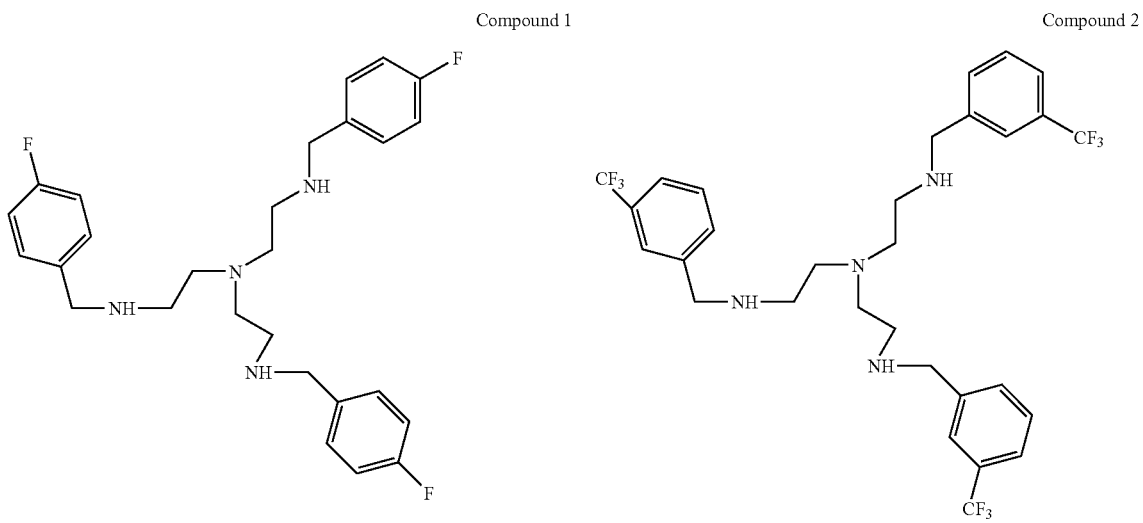

-continued
Compound 3
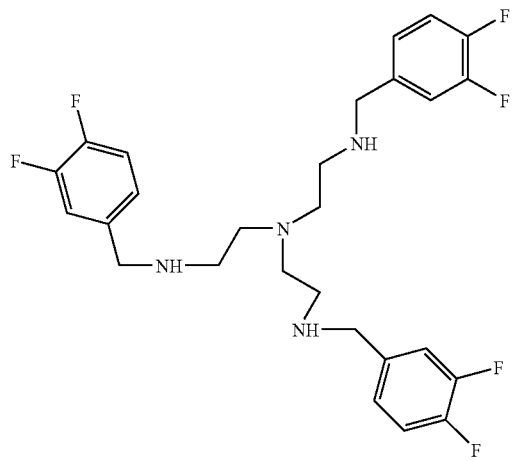
Compound 4
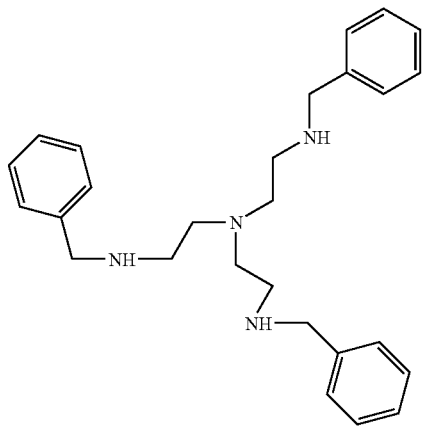
Compound 5
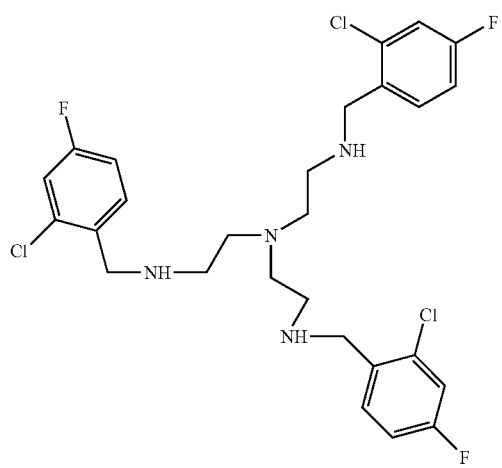
Compound 6
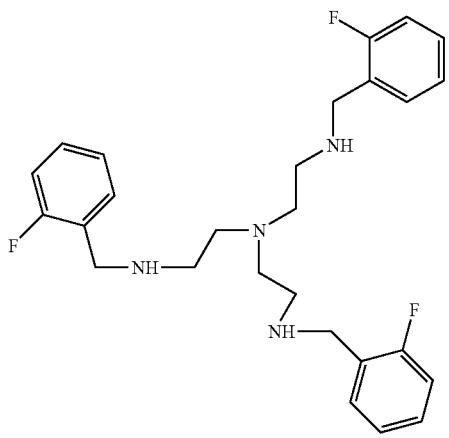
Compound 7
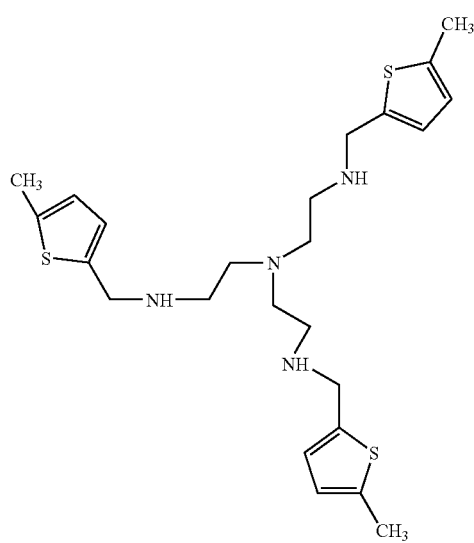
Compound 8
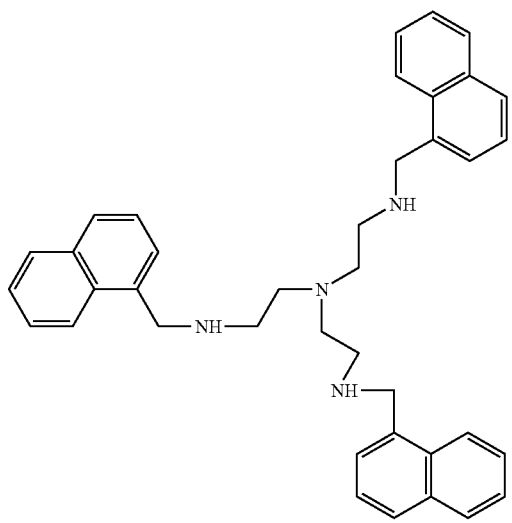

-continued
Compound 9
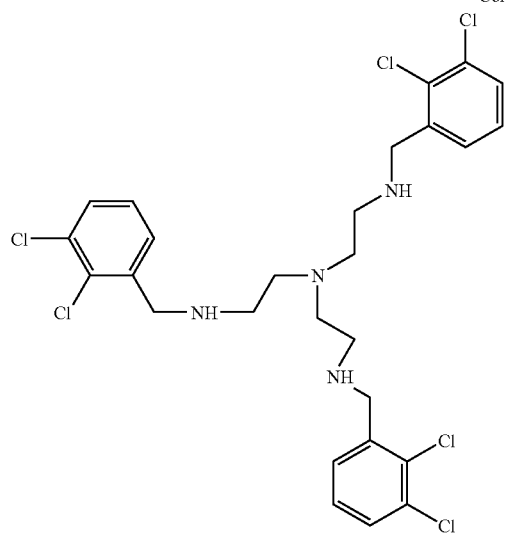
Compound 10
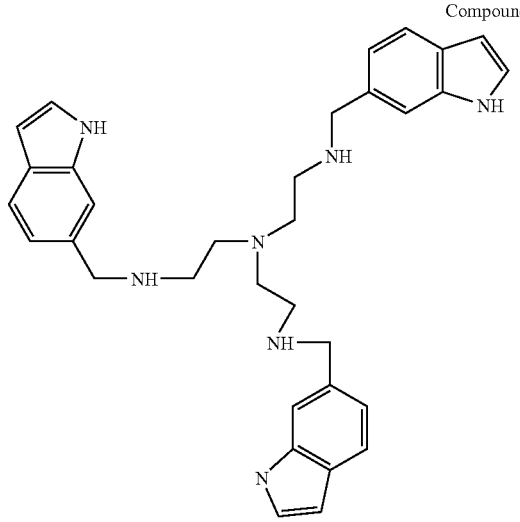
Compound 11
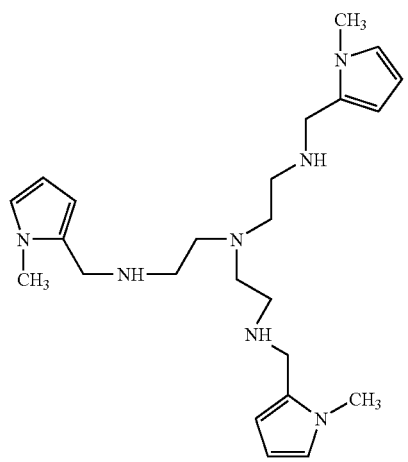
Compound 12
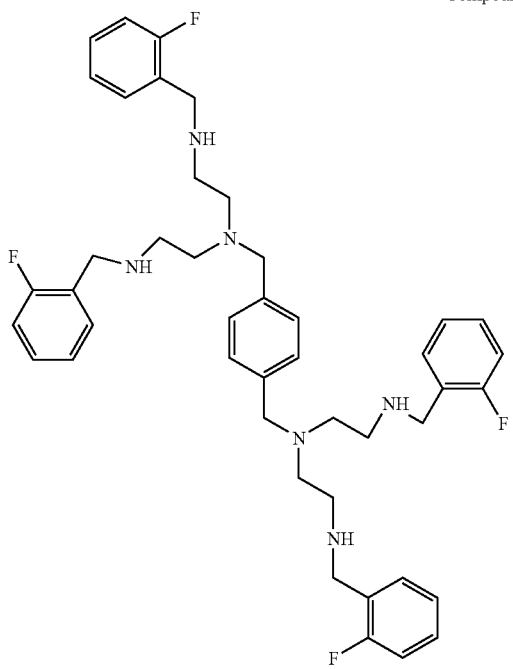

-continued
Compound 13
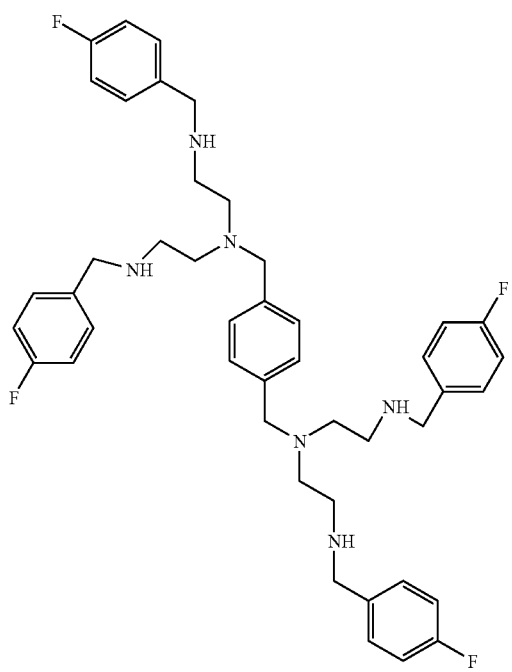
Compound 14
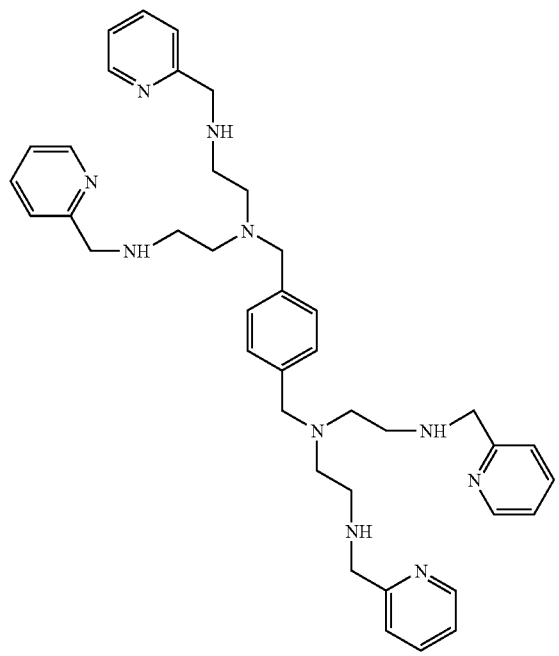
Compound 15
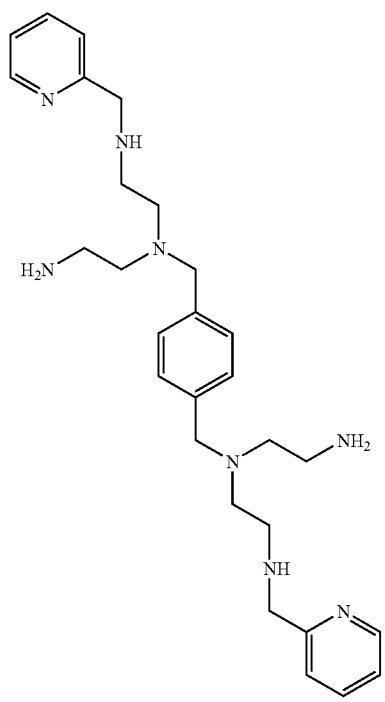
Compound 16
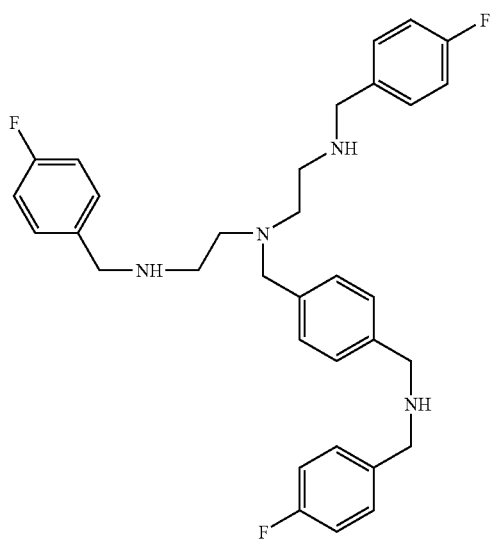

-continued
Compound 17
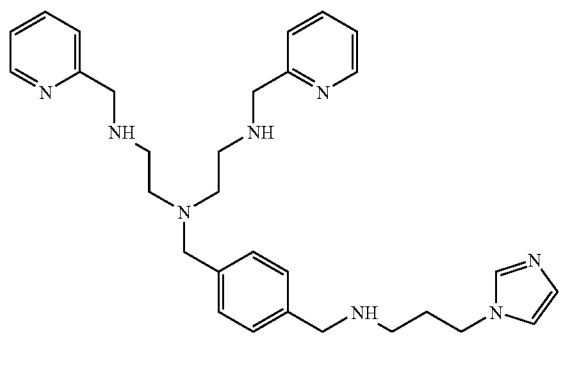
Compound 18
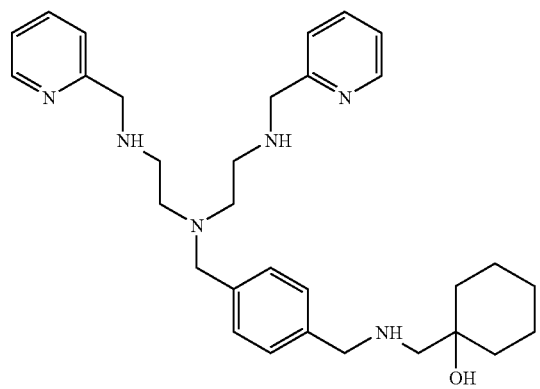
Compound 19
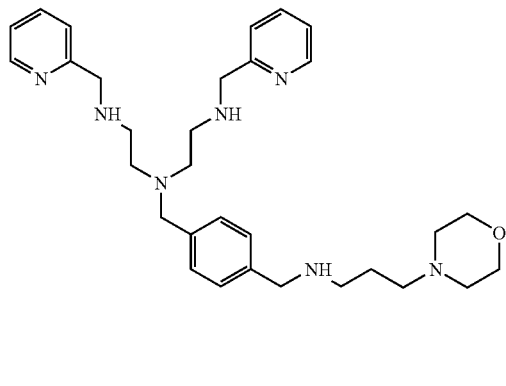
Compound 20
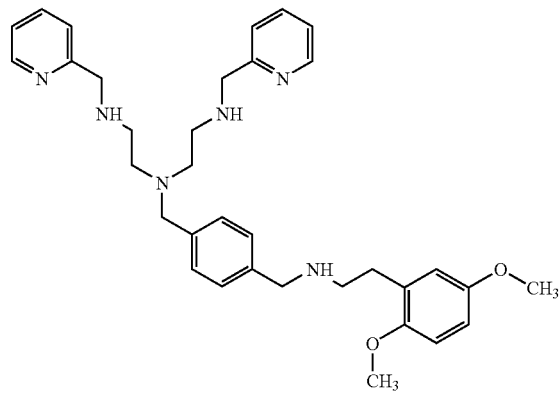
Compound 21
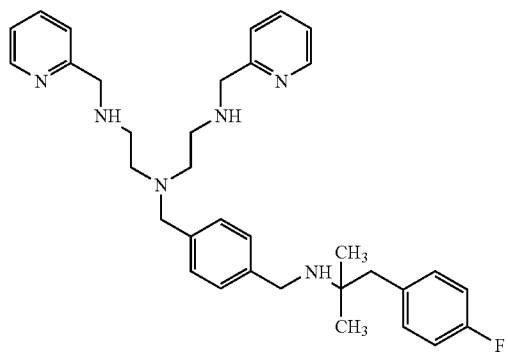
Compound 22
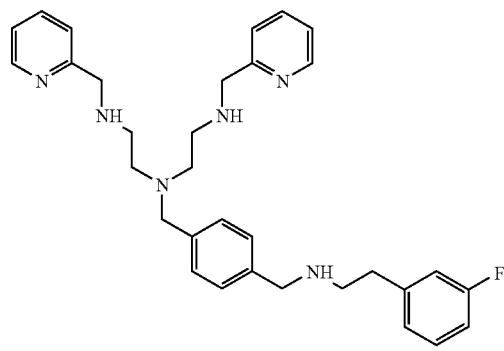
Compound 23
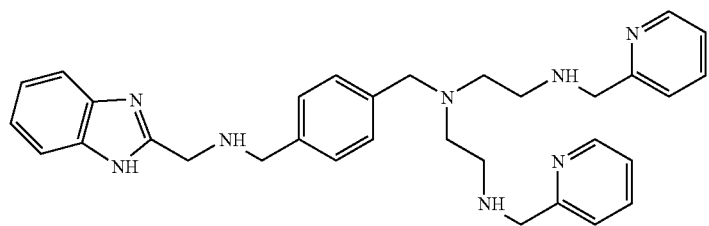

-continued
Compound 24
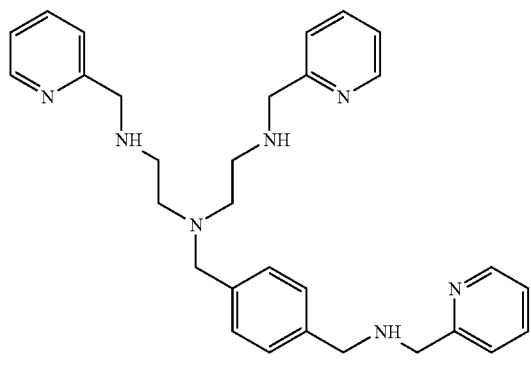
Compound 25
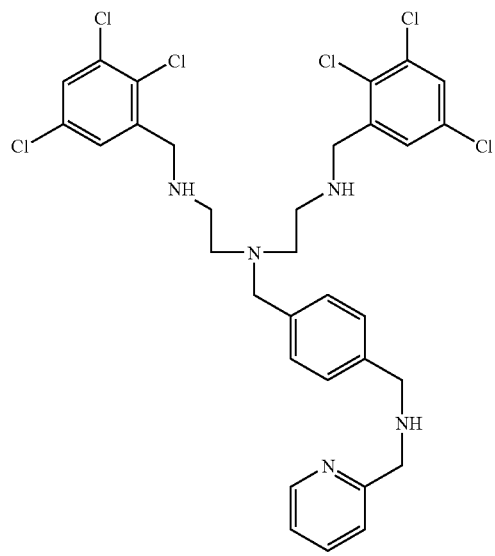
Compound 26
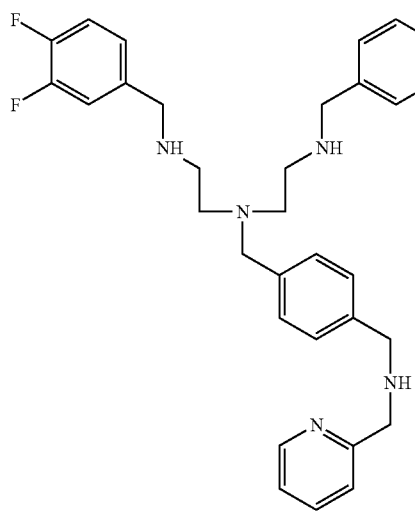
Compound 27
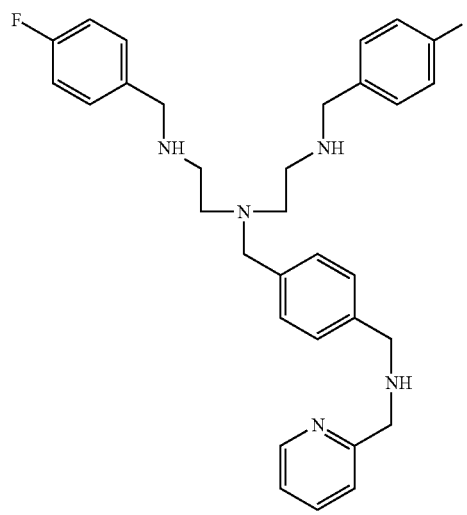
Compound 28
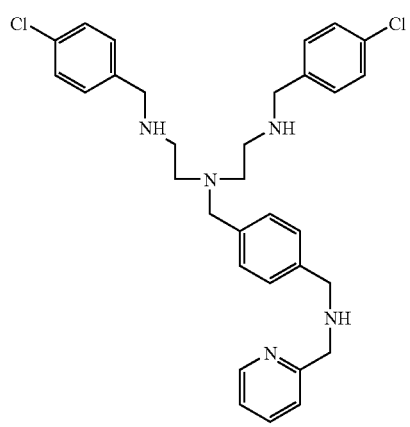
Compound 29
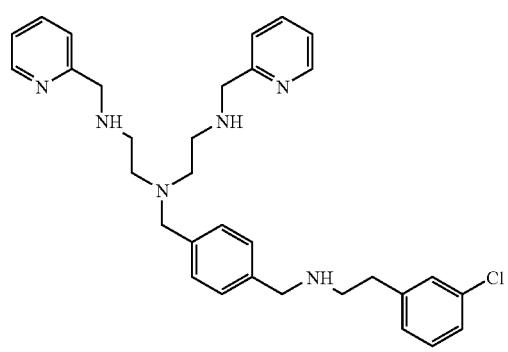

-continued
Compound 30
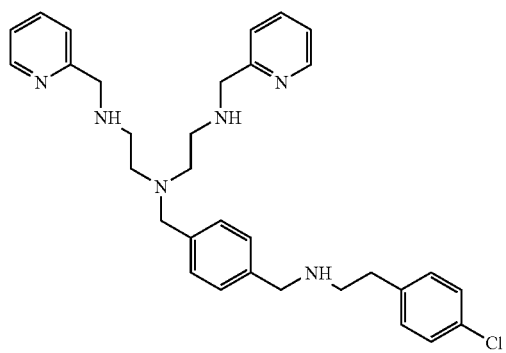
Compound 31
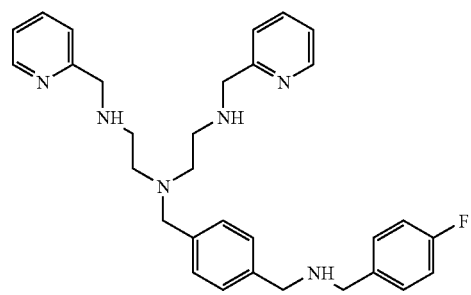
Compound 32
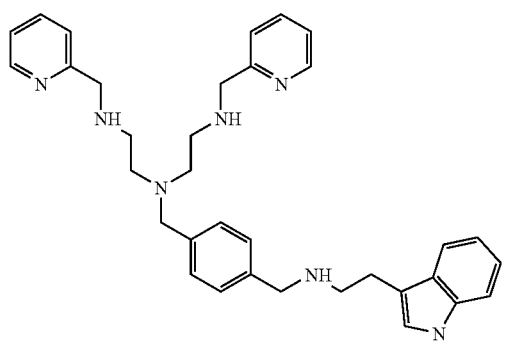
Compound 33
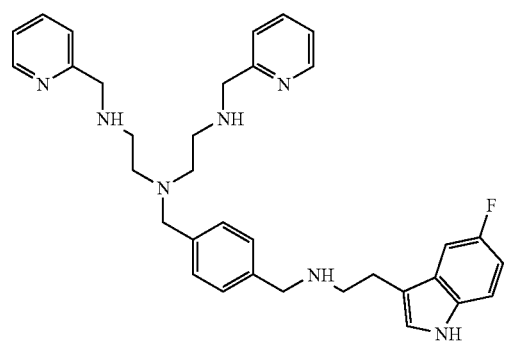
Compound 34
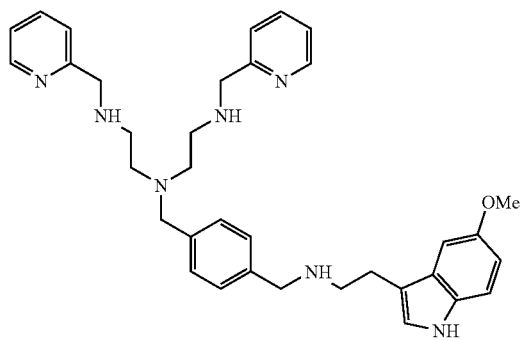
Compound 35
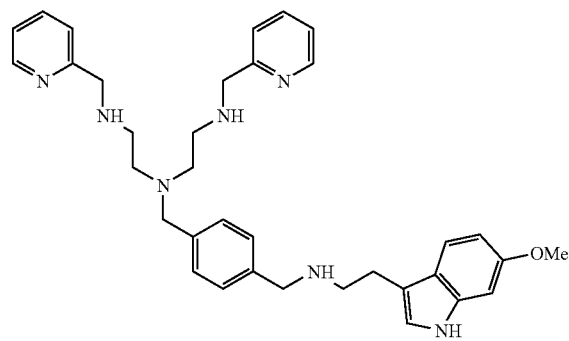
Compound 36
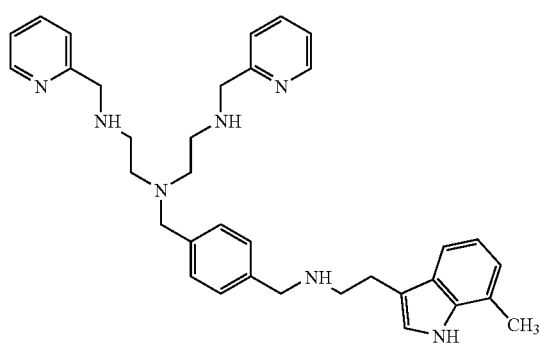
Compound 37
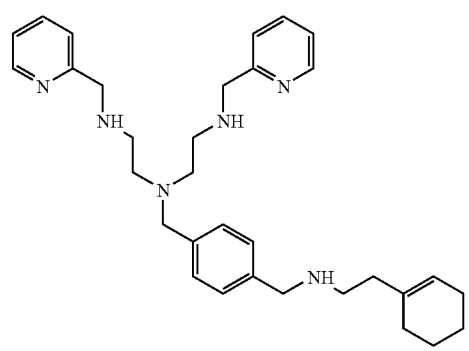

-continued
Compound 38
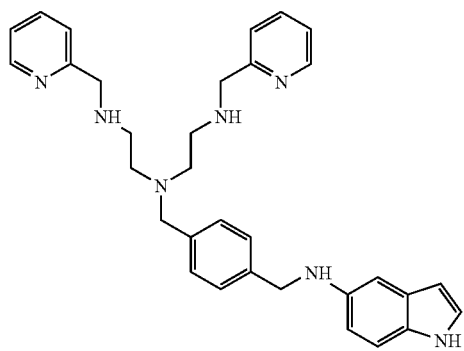
Compound 39
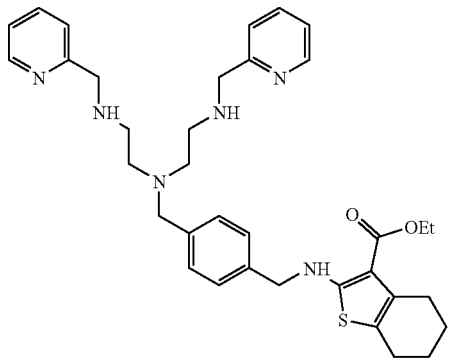
Compound 40
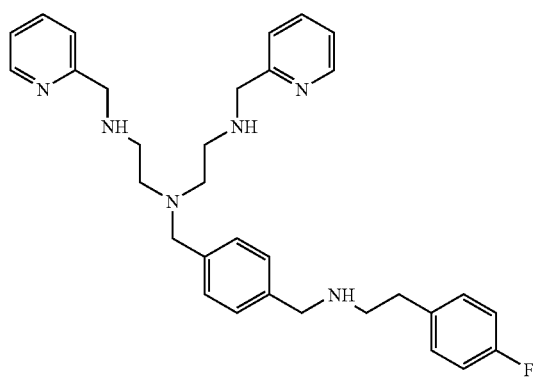
Compound 41
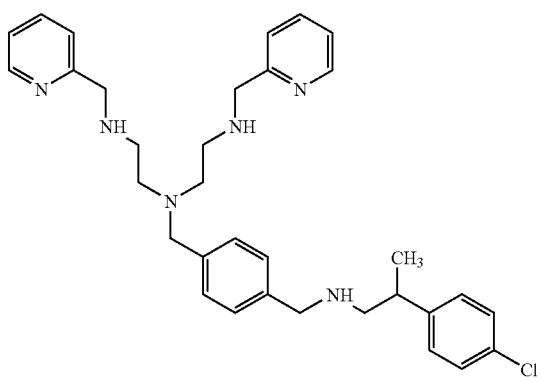
Compound 42
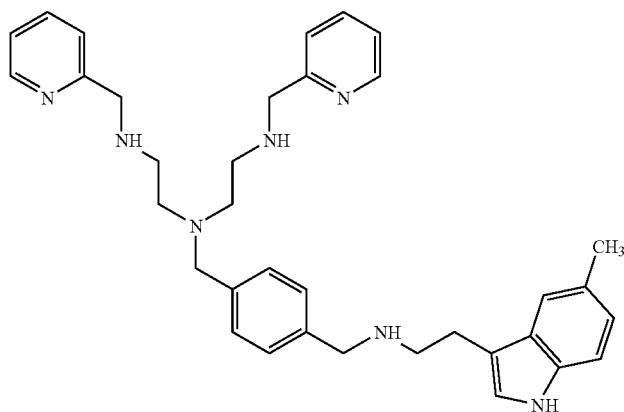
Compound 43
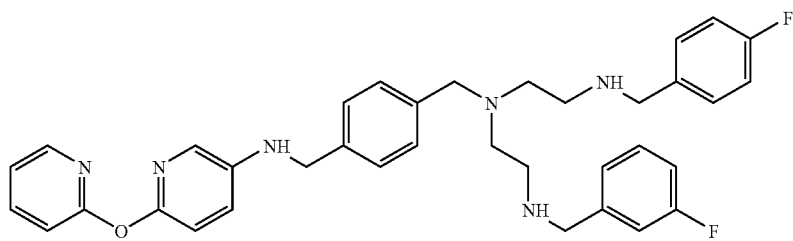

-continued
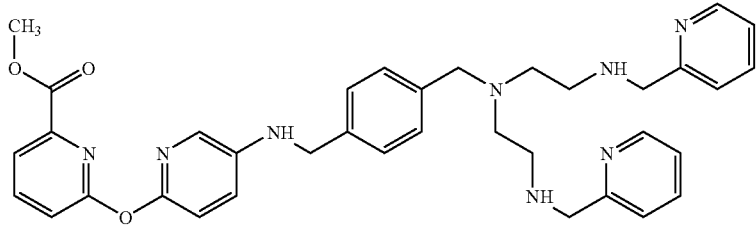
Compound 44
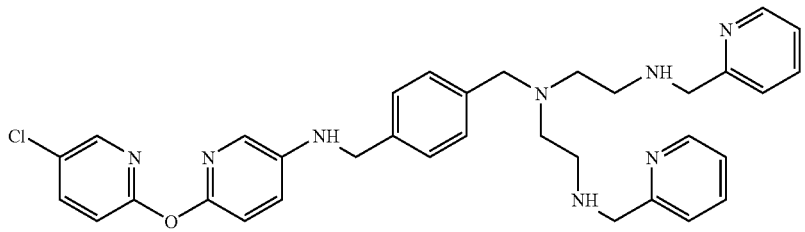
Compound 45
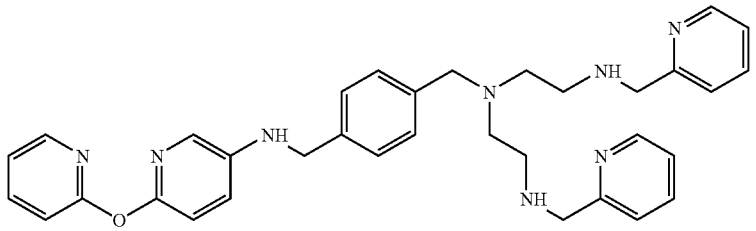
Compound 46
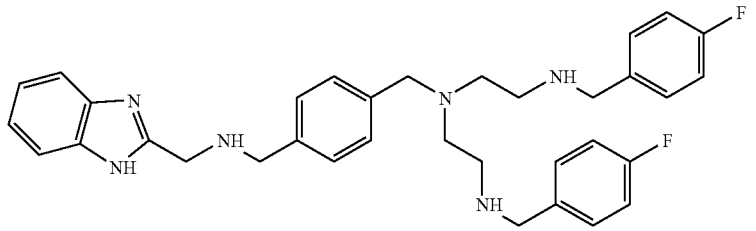
Compound 47
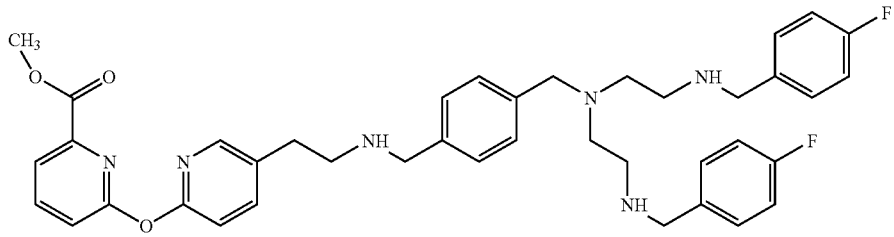
Compound 48

-continued
Compound 49
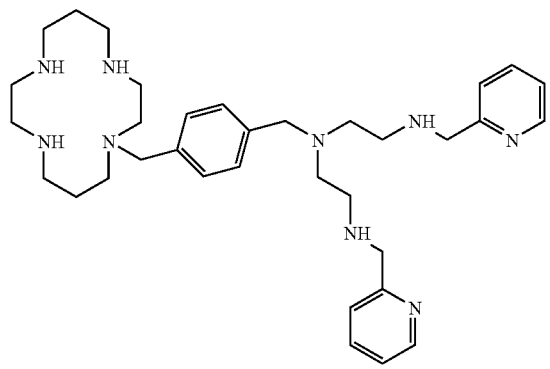
Compound 50
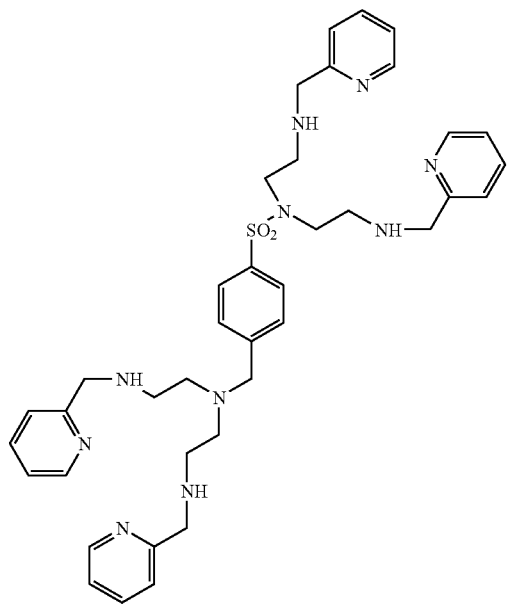
Compound 51
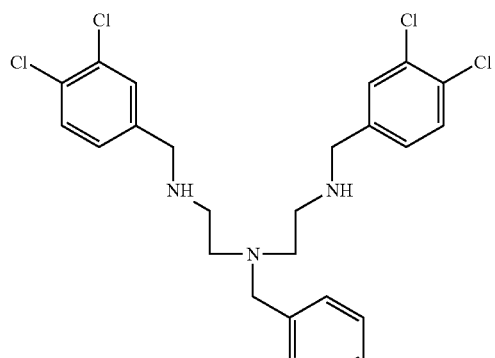
Compound 52
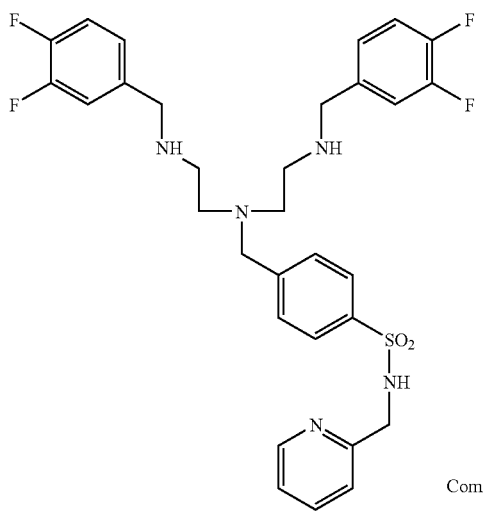
Compound 53
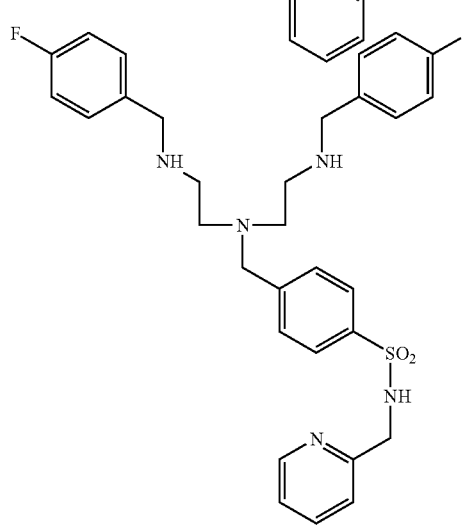
Compound 54

-continued
Compound 55
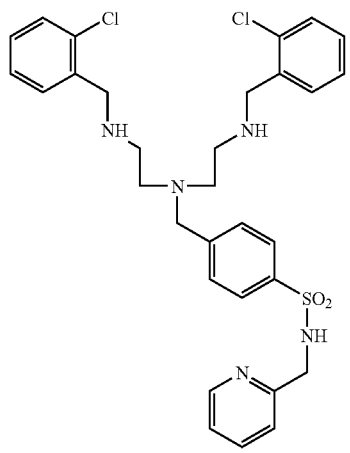
Compound 56
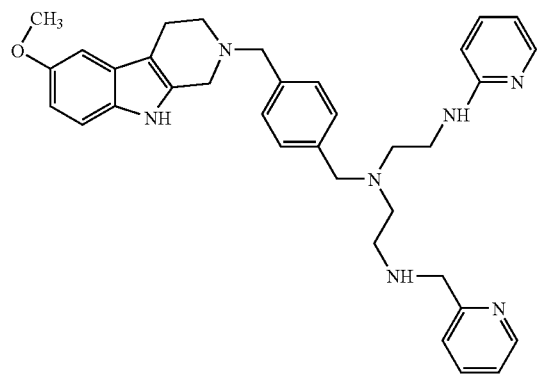
Compound 57
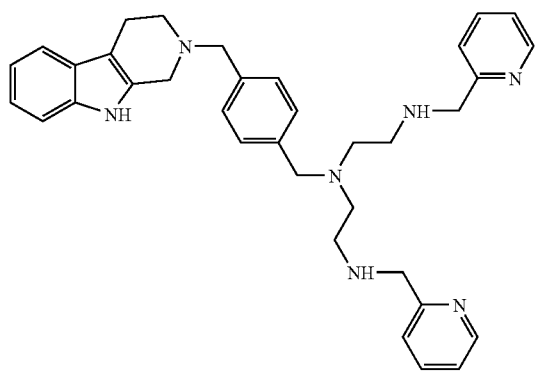
Compound 58
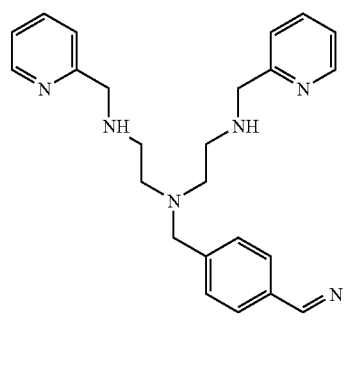
Compound 59
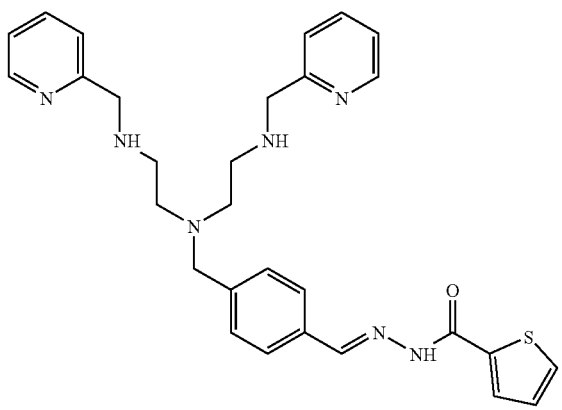
Compound 60
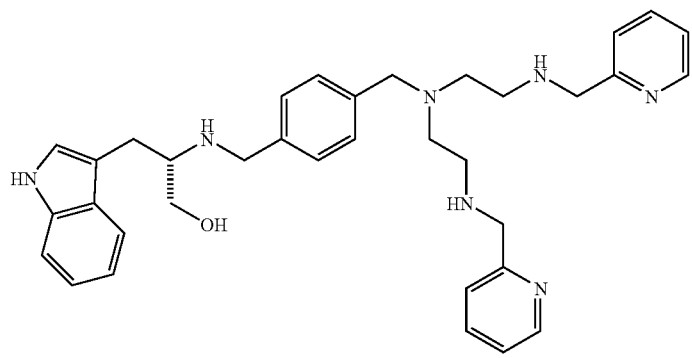

-continued
Compound 61
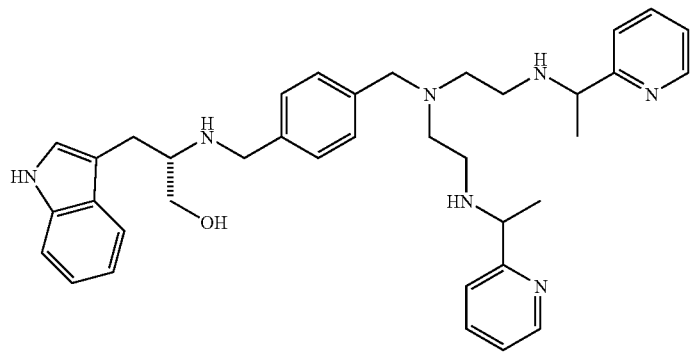
Compound 62
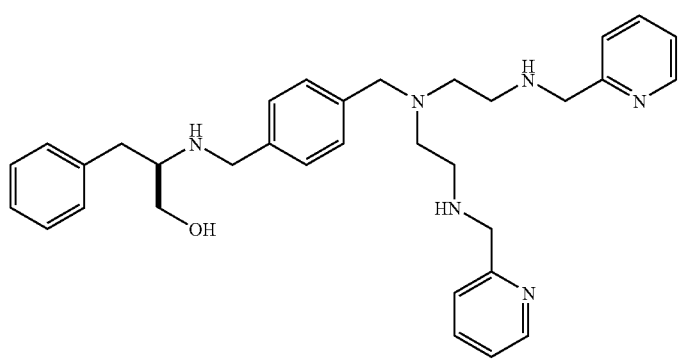
Compound 63
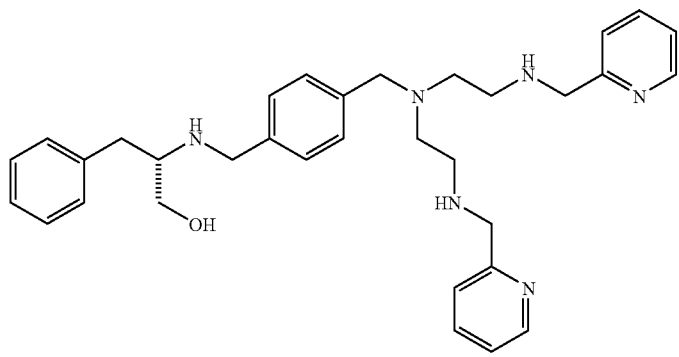
Compound 64
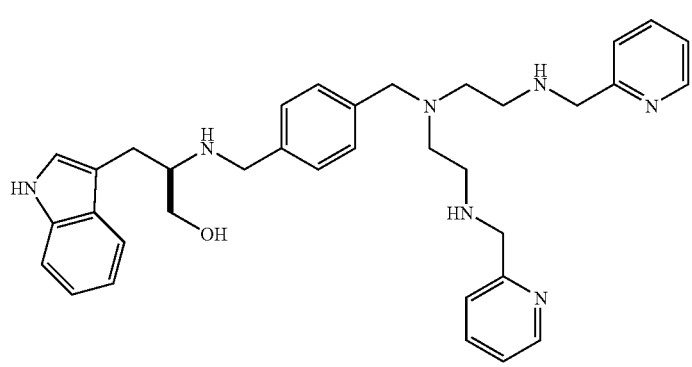

Compound 65
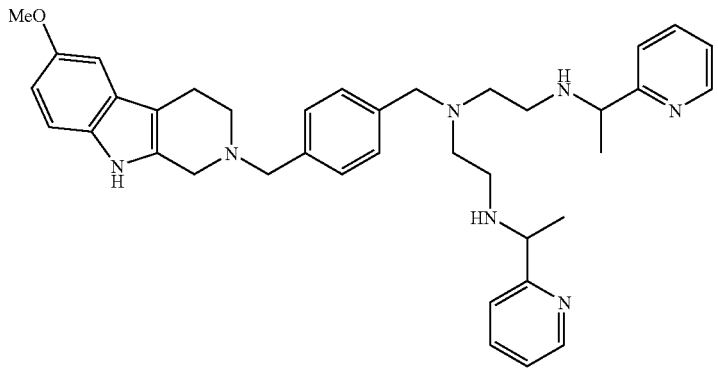
Compound 66
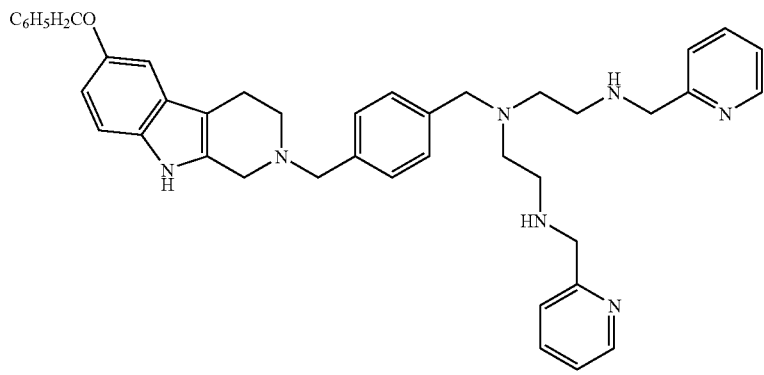
Compound 67
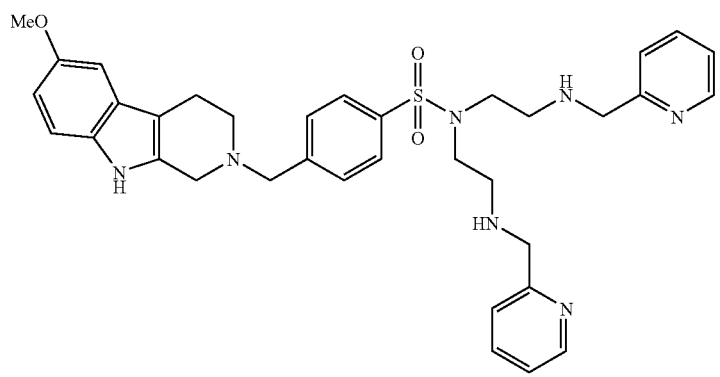
Compound 68
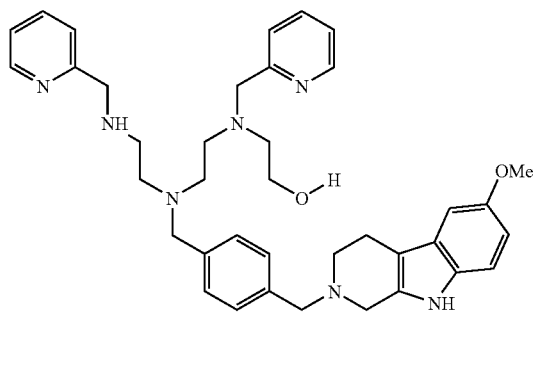
Compound 69

-continued
Compound 70
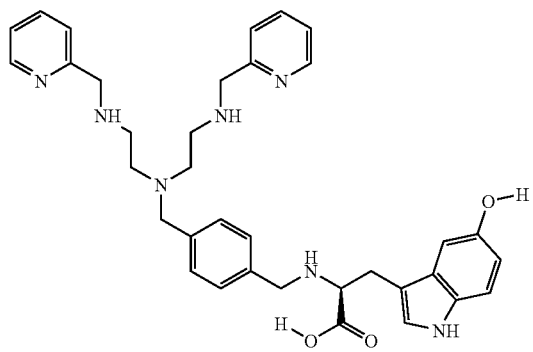
Compound 71
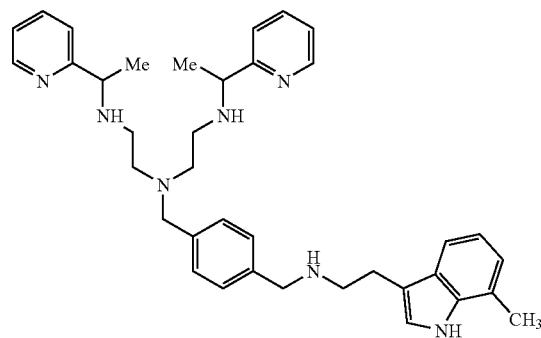
Compound 72
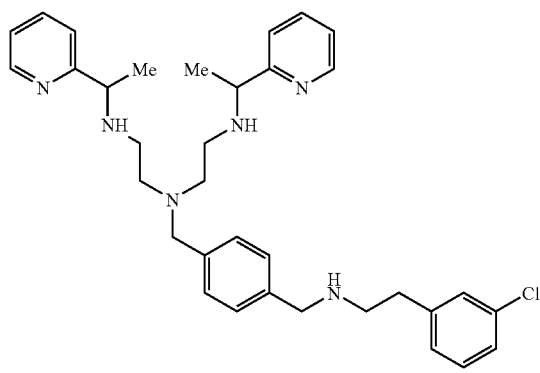
Compound 73
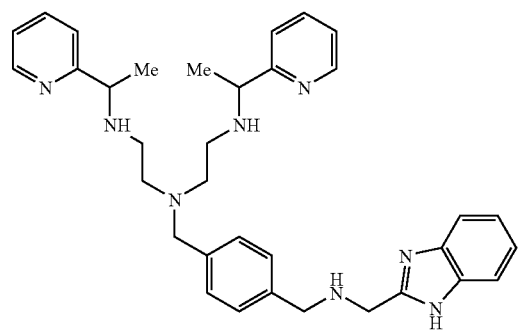
Compound 74
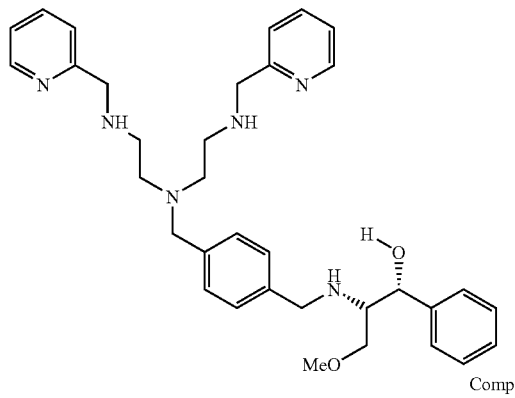
Compound 75
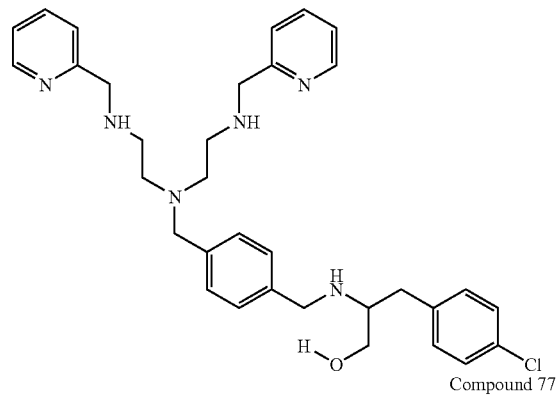
Compound 76
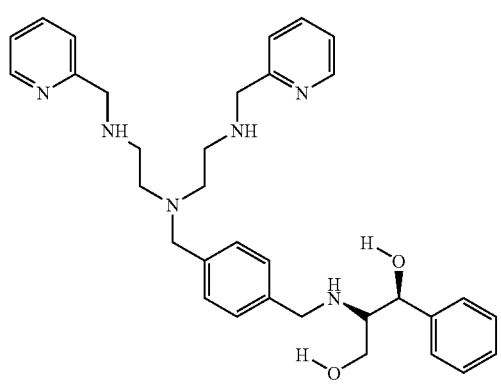
Compound 77
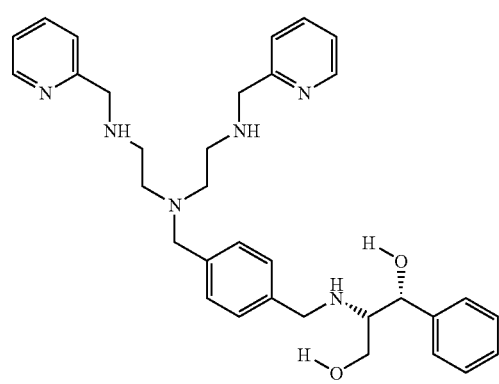

-continued
Compound 78
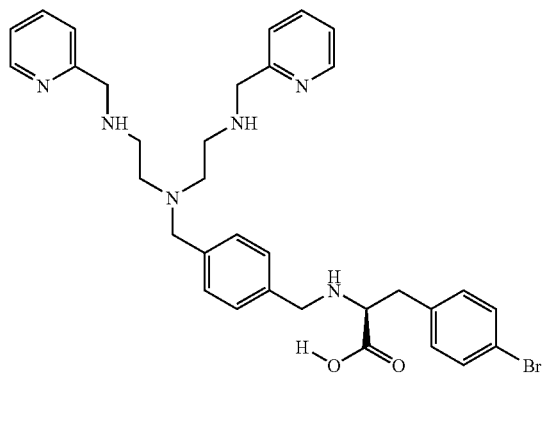
Compound 79
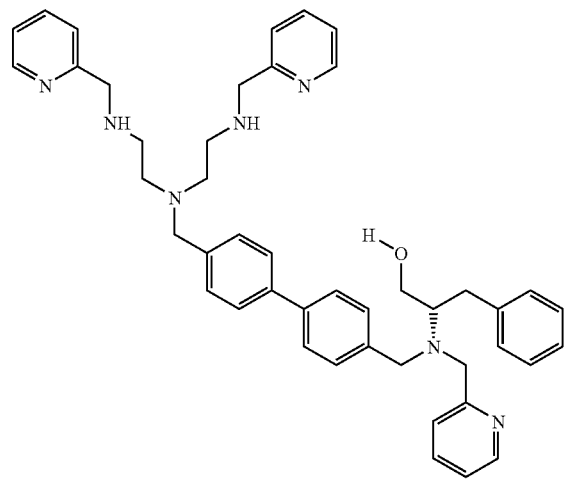
Compound 80
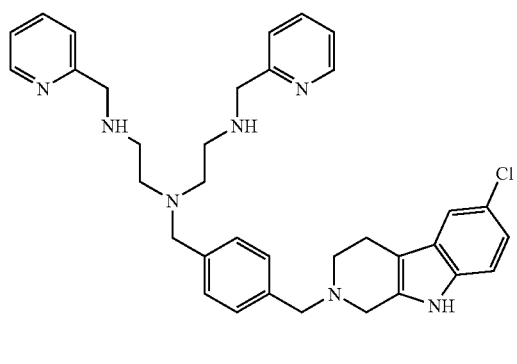
Compound 81
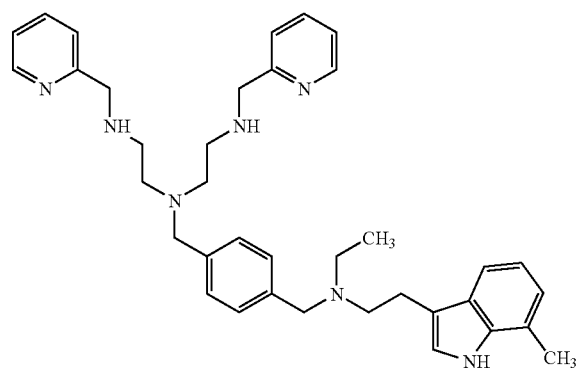
Compound 82
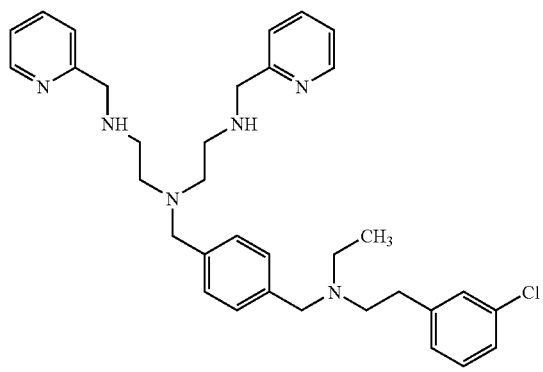
Compound 83
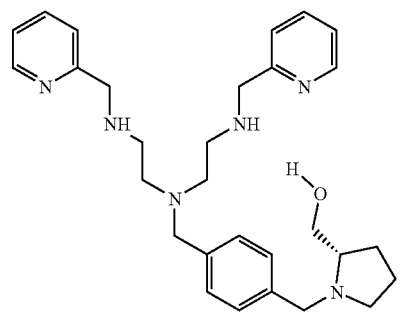

-continued
Compound 84
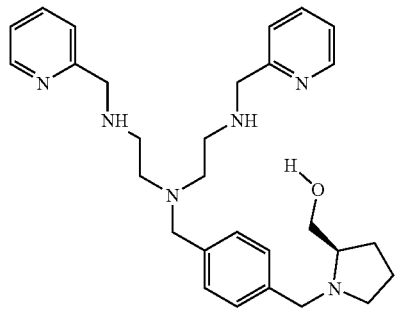
Compound 85
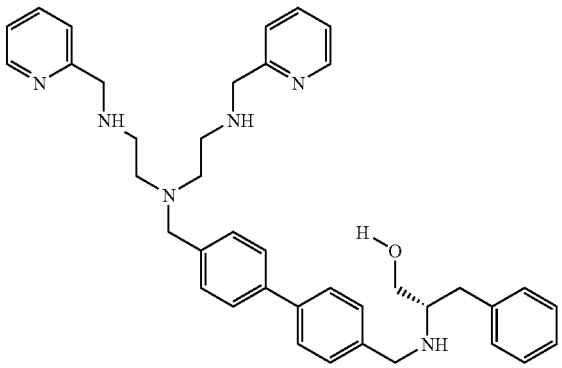
Compound 86
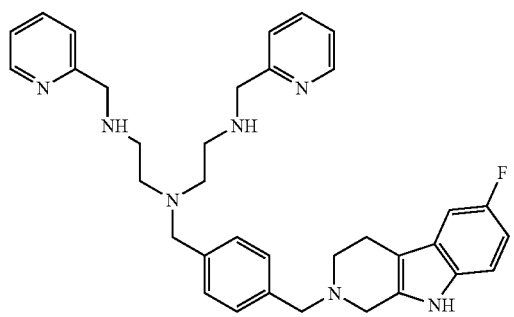
Compound 87
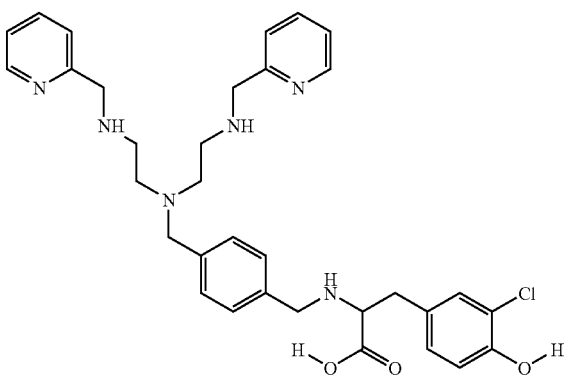
Compound 88
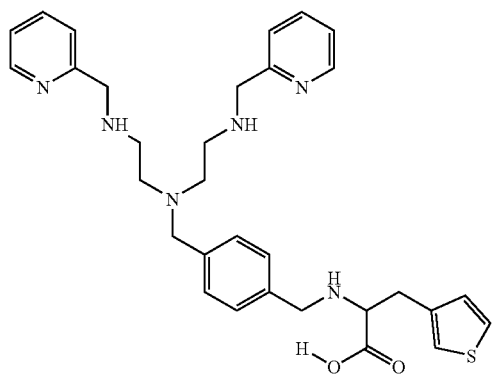
Compound 89
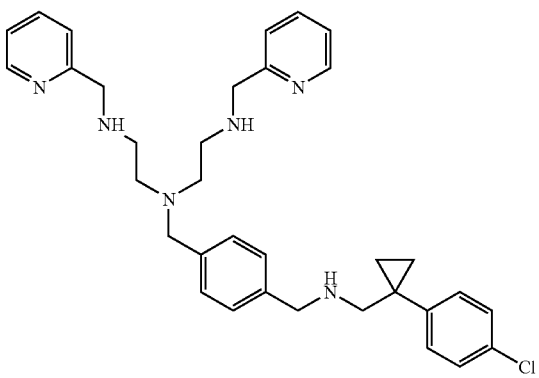
Compound 90
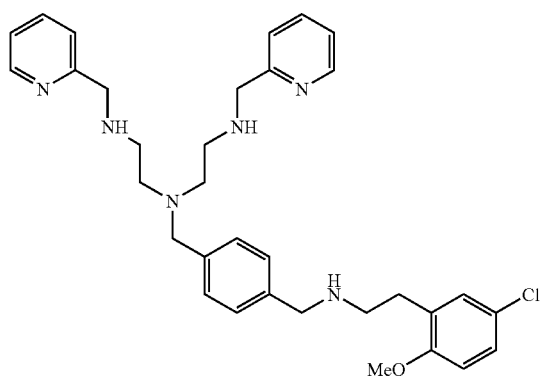
Compound 91
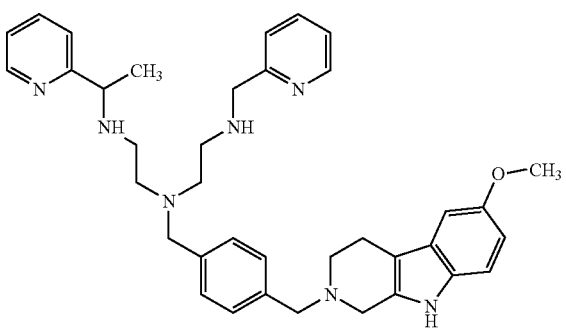

-continued
Compound 92
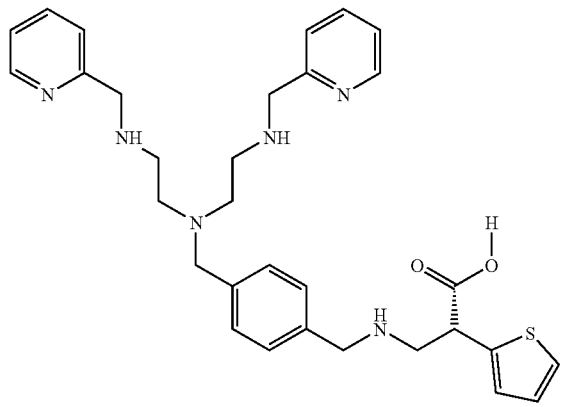
Compound 93
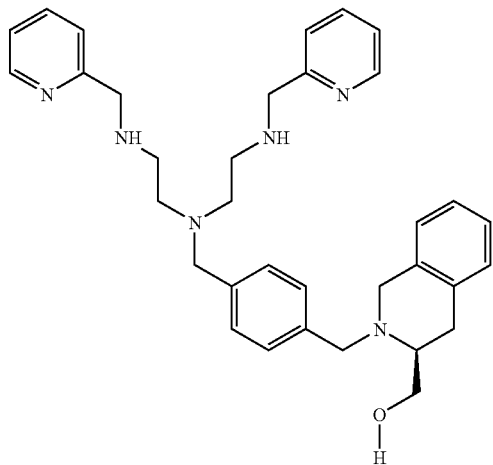
Compound 94
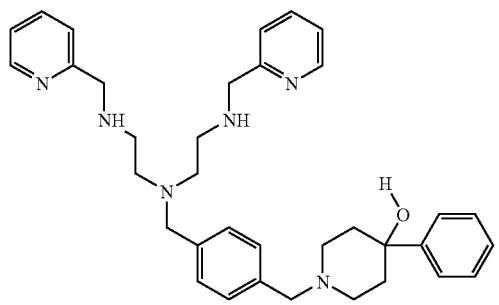
Compound 95
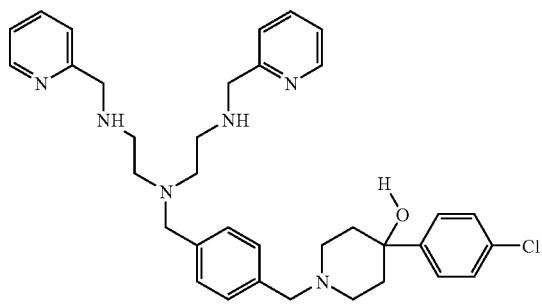
Compound 96
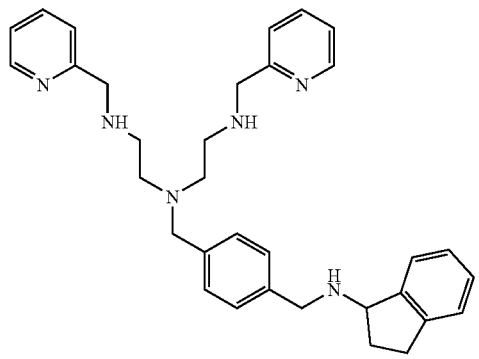
Compound 97
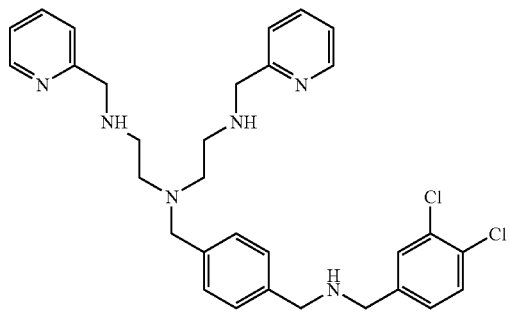
Compound 98
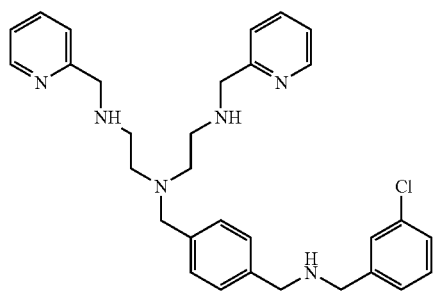
Compound 99
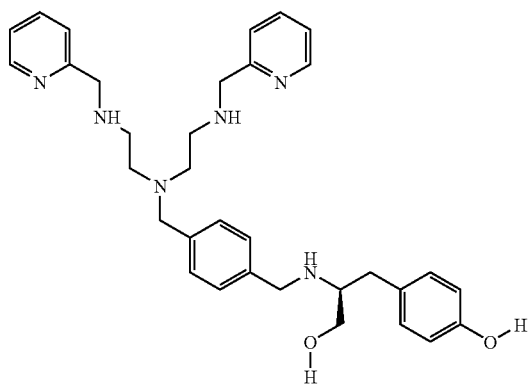

-continued
Compound 100
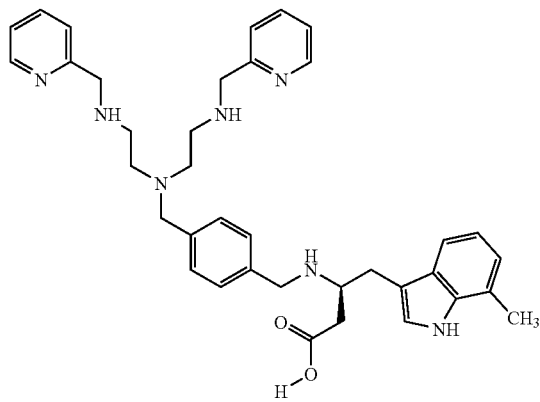
Compound 101
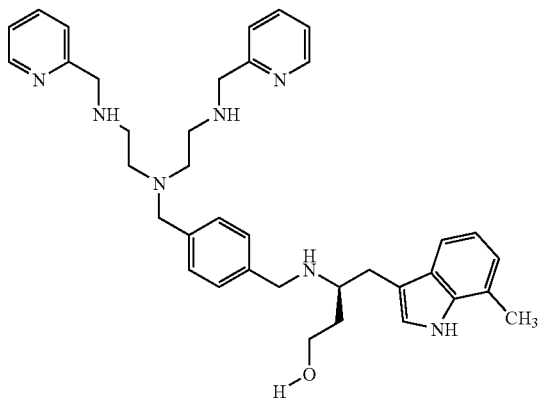
Compound 102
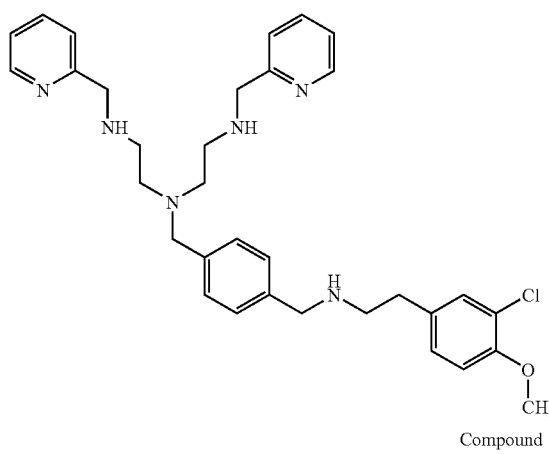
Compound 103
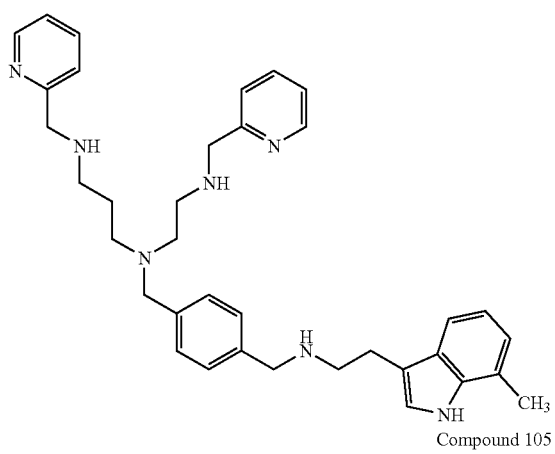
Compound 104
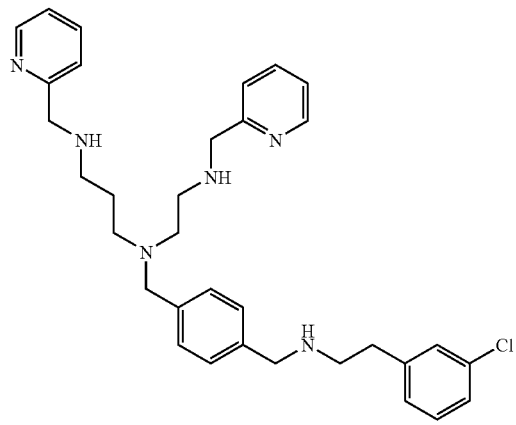
Compound 105
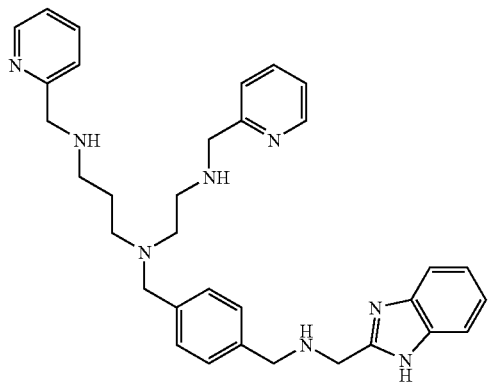
Compound 106
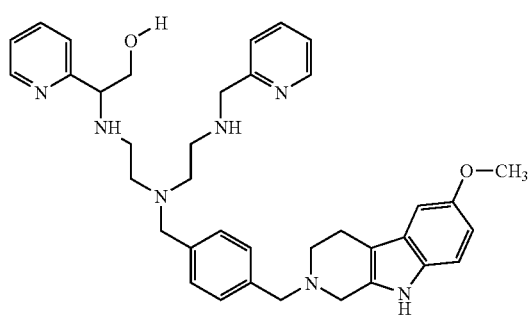
Compound 107
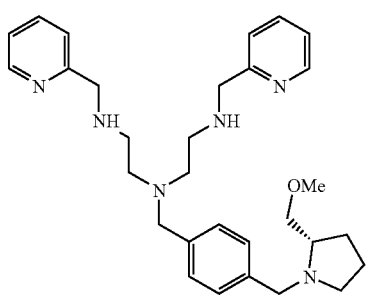

-continued
Compound 108
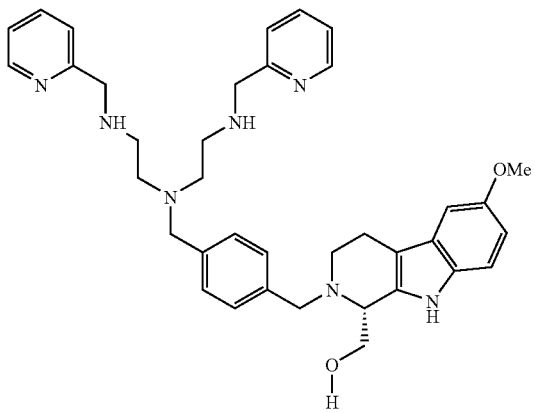
Compound 109
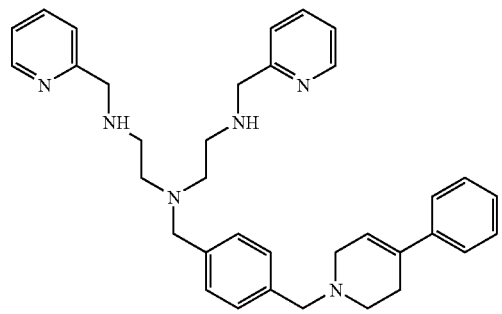
Compound 110
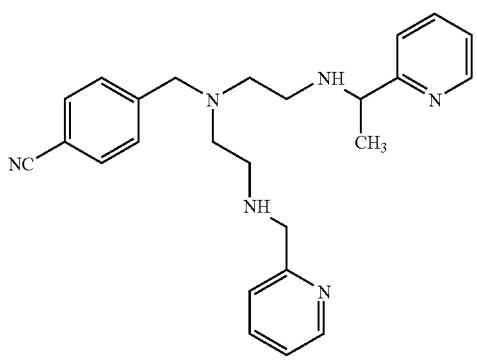
Compound 111
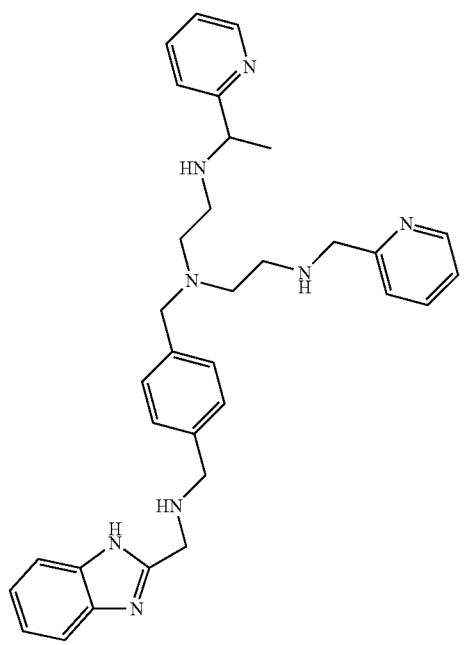
Compound 112
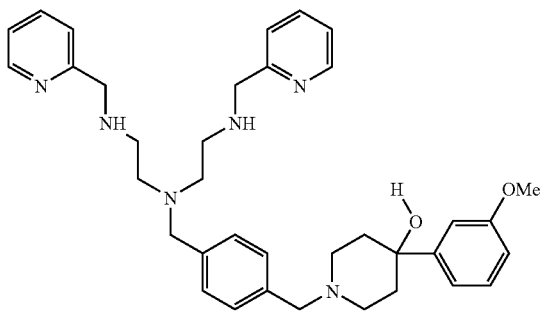
Compound 113
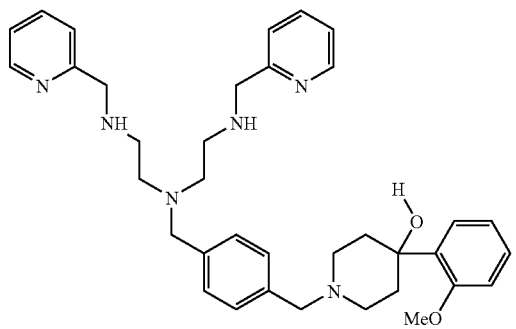

-continued
Compound 114
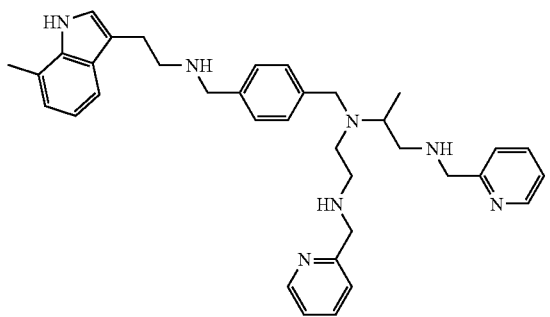
Compound 115
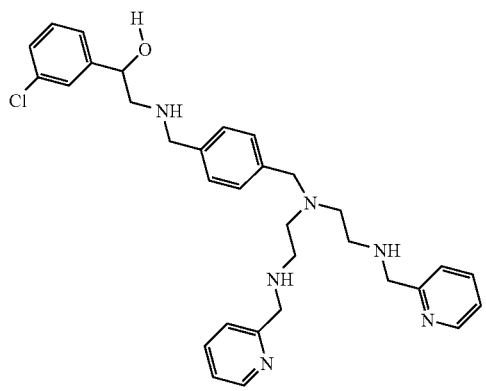
Compound 116
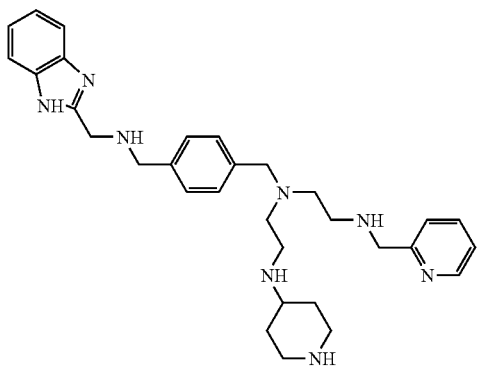
Compound 117
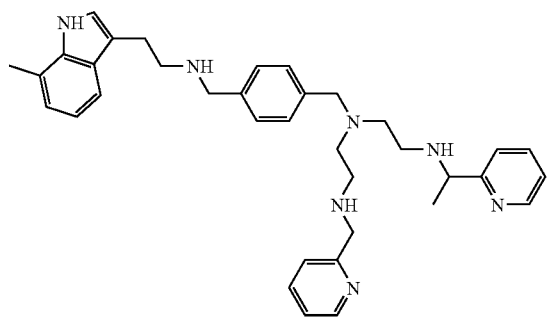
Compound 118
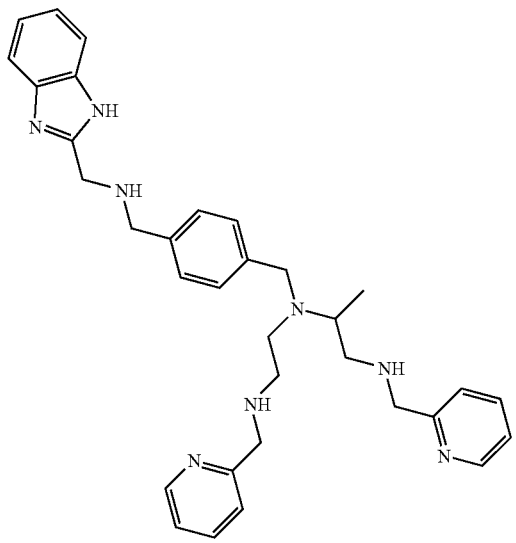
Compound 119
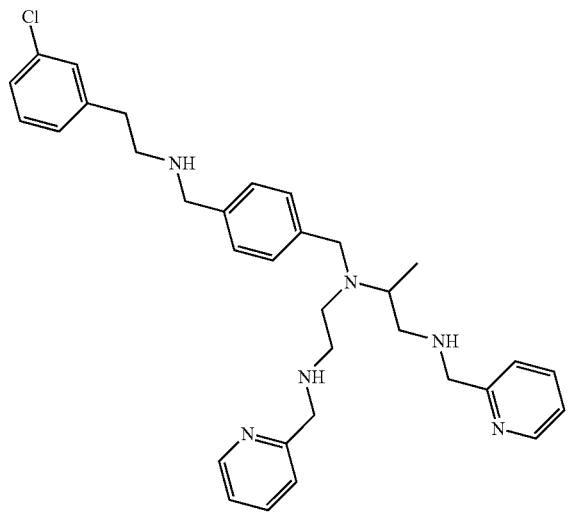

-continued
Compound 120
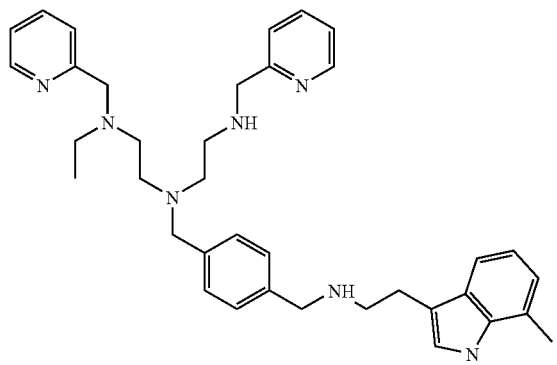
Compound 121
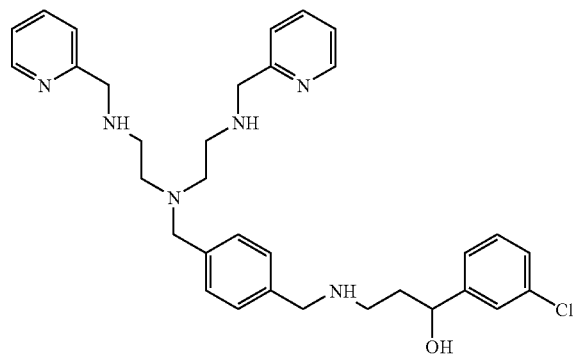
Compound 122
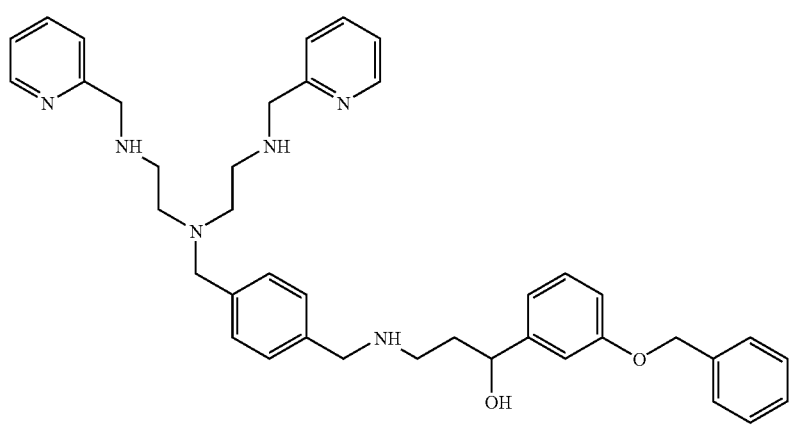
Compound 123
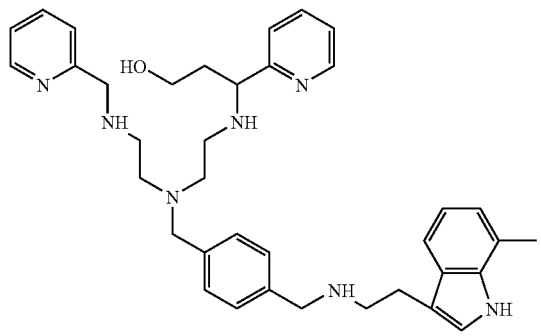
Compound 124
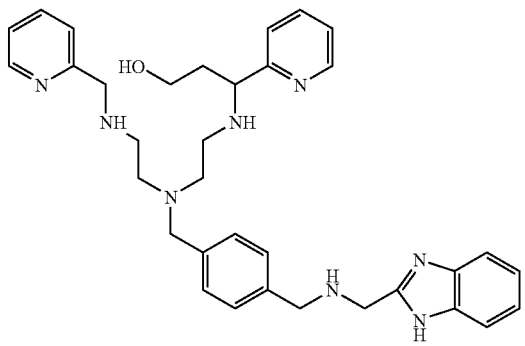
Compound 125
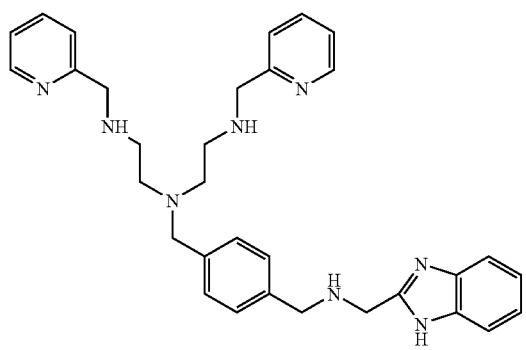
Compound 126
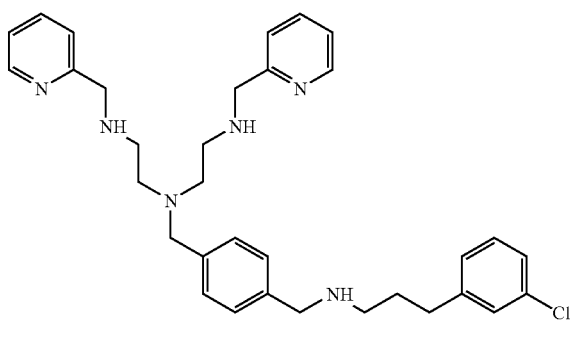

The polyamine compounds described in the summary section above can be prepared by methods well known in the art, including the synthetic routes disclosed herein.

For example, compound 1-11 can be respectively prepared by reacting tris(2-aminoethyl)amine with three equivalent amounts of a corresponding aldehyde, and followed by a reduction reaction using sodium borohydride.

In another example, one can react 1,4-dibromoxylene with two equivalent amounts of bis(t-butoxycarbonylaminoethyl) amine. The reaction mixture is subsequently treated with hydrochloric acid to give an intermediate, 1,4-di[bis(2-aminoethyl)aminomethyl]benzene. This intermediate can react with four equivalent amounts of corresponding aldehyde compounds and sodium borohydride to give compounds 12-14. Alternatively, this intermediate can react with two equivalent amounts of pyridine-2-carbaldehyde, and then with sodium borohydride to give compound 15. One can also react 1,4-dibromoxylene with one equivalent amount of bis (t-butoxycarbonylaminoethyl)amine and one equivalent amount of other amine compounds. Compounds 56-57, 65, 66, 68, 80, 86, 91, 93-95, and 106-109 can be prepared through this synthetic route, followed by sequential treatments with hydrochloric acid, two equivalent amounts of a corresponding aldehyde, and sodium borohydride. In a similar manner, compounds 49 can be prepared by reacting 1,4-dibromoxylene with one equivalent amount of tri-t-butoxycarbonyl protected cyclam and one equivalent amount of bis(2-pyridiyliminoethyl)amine, followed by a reduction reaction using sodium borohydride.

In another example, compounds 16-48, 58-64, 69-79, 81-85, 87-90, 92, 96-105, 115, 121, 122, 125, and 126 can be synthesized using the following synthetic route. One can react 4-cyanobenzylbromide with one equivalent amount of bis(t-butoxycarbonylaminoethyl)amine and then hydrochloric acid to give 4-[bis(2-aminoethyl)amino-methyl]-benzonitrile. This benzonitrile can then be treated sequentially with two equivalent amounts of an aldehyde, methyl]-benzaldehyde. The just-mentioned compounds can then be prepared by treating this benzaldehyde sequentially with one equivalent amount of a corresponding amine, sodium borohydride, and hydrochloric acid. Compounds 110, 111, 116, 117, 120, 123, and 124 can be prepared in a similar manner except that the benzonitrile is treated with one equivalent amount of an aldehyde and one equivalent amount of a ketone.

In another example, one can react 4-bromomethylbenzenesulfonyl chloride with one equivalent amount of an amine and then one equivalent amount of bis(t-butoxycarbonylaminoethyl)amine. An intermediate is then obtained after treating the above reaction mixture with hydrochloric acid. Compounds 51-55 can then be respectively prepared by treating this intermediate with a corresponding aldehyde and followed with sodium borohydride. Compounds 50, 67, 112, and 113 can be prepared using the same procedure as that of compounds 51-55 except that 4-bromomethylbenzenesulfonyl chloride is treated with two equivalent amounts of bis(t-butoxycarbonylaminoethyl)amine.

In another example, one can react 4-cyanobenzaldehyde sequentially with one equivalent amount of 2-methyl-2-aminoethanol, sodium borohydride, and 2-(2-bromo-ethoxy)-tetrahydro-pyran to obtain a substituted aminomethylbenzonitrile. Upon removal the tetrahydropyranyl protection group, the benzonitrile can be sequentially mesylated and treated with 2-aminomethylpyridine. After the resultant secondary amine is protected, the benzonitrile can then be treated with diisobutylaluminum, one equivalent amount of a corresponding amine, sodium borohydride, triflic acid, and hydrochloric acid to obtain compounds 114, 118, and 119.

A polyamine compound thus synthesized can be further purified by a method such as column chromatography, high-pressure liquid chromatography, or recrystallization.

Other polyamine compounds can be prepared using other suitable starting materials through the above synthetic routes and others known in the art. The methods described above may also additionally include steps, either before or after the steps described specifically herein, to add or remove suitable protecting groups in order to ultimately allow synthesis of the polyamine compounds. In addition, various synthetic steps may be performed in an alternate sequence or order to give the desired compounds. Synthetic chemistry transformations and protecting group methodologies (protection and deprotection) useful in synthesizing applicable polyamine compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The polyamine compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one polyamine compound described above and a pharmaceutical acceptable carrier. Further, this invention covers a method of administering an effective amount of one or more of the polyamine compounds to a patient having a disease described in the summary section above. This invention also covers a method of administering an effective amount of one or more of the polyamine compounds for enhancing migration of bone marrow-derived cells to blood. "An effective amount" refers to the amount of an active polyamine compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more polyamine compounds can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active polyamine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active polyamine compound. Examples of other carriers include colloidal silicon oxide, magnesium stearate, cellulose, sodium lauryl sulfate, and D&C Yellow #10.

The polyamine compounds described above can be preliminarily screened for their efficacy in treating above-described diseases by an in vitro assay (See Example 127 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1: N-(4-fluoro-benzyl)-N',N'-bis-[2-(4-fluoro-benzylamino)-ethyl]-ethane-1,2-diamine Tris(2-aminoethyl)amine (0.01 mol) and 4-fluoro-benzaldehyde (0.03 mol) were dissolved in MeOH (50 mL). After stirring at 25° C. for 15 h, NaBH$_4$ (1.90 g, 0.05 mol) was added to the above solution at 0° C. The reaction mixture was stirred for 2 h at 25° C. It was then diluted with CH$_2$Cl$_2$ (100 mL) and ammonium chloride aqueous solution (10%, 70 mL). The organic layer was separated, washed with water (100 mL), dried over MgSO$_4$ (s), and concentrated under reduced pressure to yield an oil product. The crude product was purified using alumina column chromatography (EtOAc/MeOH=8:2) to afford compound 1.

LC/MS (M$^+$+1): 471.

EXAMPLE 2

Preparation of Compound 2: N-(3-trifluoromethyl-benzyl)-N',N'-bis-[2-(3-trifluoromethyl-benzylamino)-ethyl]-ethane-1,2-diamine Compound 2 was prepared in a manner similar to that described in Example 1.

LC/MS (M$^+$+1): 621.

EXAMPLE 3

Preparation of Compound 3: N-(3,4-difluoro-benzyl)-N',N'-bis-[2-(3,4-difluoro-benzylamino)-ethyl]-ethane-1,2-diamine Compound 3 was prepared in a manner similar to that described in Example 1.

LC/MS (M$^+$+1): 525.

EXAMPLE 4

Preparation of Compound 4: N-benzyl-N',N'-bis-(2-benzylamino-ethyl)-ethane-1,2-diamine Compound 4 was prepared in a manner similar to that described in Example 1.

LC/MS (M$^+$+1): 417.

EXAMPLE 5

Preparation of Compound 5: N-(2-chloro-4-fluoro-benzyl)-N',N'-bis-[2-(2-chloro-4-fluoro-benzylamino)-ethyl]-ethane-1,2-diamine Compound 5 was prepared in a manner similar to that described in Example 1.

LC/MS (M$^+$+1): 574.

EXAMPLE 6

Preparation of Compound 6: N-(2-fluoro-benzyl)-N',N'-bis-[2-(2-fluoro-benzylamino)-ethyl]-ethane-1,2-diamine Compound 6 was prepared in a manner similar to that described in Example 1.

LC/MS (M$^+$+1): 471.

EXAMPLE 7

Preparation of Compound 7: N-(5-methyl-thiophen-2-ylmethyl)-N',N'-bis-{2-[(5-methyl-thiophen-2-ylmethyl)-amino]-ethyl}-ethane-1,2-diamine Compound 7 was prepared in a manner similar to that described in Example 1.

LC/MS (M$^+$+1): 477.

EXAMPLE 8

Preparation of Compound 8: N-naphthalen-1-ylmethyl-N',N'-bis-{2-[(naphthalen-1-ylmethyl)-amino]-ethyl}-ethane-1,2-diamine Compound 8 was prepared in a manner similar to that described in Example 1.
LC/MS (M$^+$+1): 567.

EXAMPLE 9

Preparation of Compound 9: N-(2,3-dichloro-benzyl)-N',N'-bis-[2-(2,3-dichloro-benzylamino)-ethyl]-ethane-1,2-diamine Compound 9 was prepared in a manner similar to that described in Example 1.
LC/MS (M$^+$+1): 624.

EXAMPLE 10

Preparation of Compound 10: N-(1H-indol-6-ylmethyl)-N',N'-bis-{2-[(1H-indol-6-ylmethyl)-amino]-ethyl}-ethane-1,2-diamine Compound 10 was prepared in a manner similar to that described in Example 1.
LC/MS (M$^+$+1): 534.

EXAMPLE 11

Preparation of Compound 11: N-(1-methyl-1H-pyrrol-2-ylmethyl)-N',N'-bis-{2-[(1-methyl-1H-pyrrol-2-ylmethyl)-amino]-ethyl}-ethane-1,2-diamine Compound 11 was prepared in a manner similar to that described in Example 1.
LC/MS (M$^+$+1): 426.

EXAMPLE 12

Preparation of Compound 12: N-[4-({bis-[2-(2-fluoro-benzylamino)-ethyl]-amino}-methyl)-benzyl]-N'-(2-fluoro-benzyl)-N-[2-(2-fluoro-benzylamino)-ethyl]-ethane-1,2-diamine 1,4-Dibromoxylene (0.012 mol) was treated with bis(tert-butoxyaminoethyl)amine (0.024 mol) in the presence of K$_2$CO$_3$ (0.5 mol) in CH$_3$CN (60 mL) at 60° C. After stirring for 12 h, the solution was allowed to cool down to room temperature, filtered, and concentrated. The concentrate was then treated with HCl/ether and neutralized with K$_2$CO$_3$ to afford 1,4-di[bis(2-aminoethyl)amino-methyl]benzene quantitatively.

1,4-Di[bis(2-aminoethyl)amino-methyl]benzene (0.01 mol) thus obtained and 4-fluoro-benzaldehyde (0.04 mol) were dissolved in MeOH (50 mL). After stirring at 25° C. for 15 h, NaBH$_4$ (2.28 g, 0.06 mol) was added at 0° C. to the above solution. The reaction mixture was stirred for another 2 h at 25° C. It was then diluted with CH$_2$Cl$_2$ (100 mL) and ammonium chloride aqueous solution (10%, 70 mL). The organic layer was separated, washed with water (100 mL), dried over MgSO$_4$ (s), and concentrated under reduced pressure to yield an oil product. The crude product was purified using alumina column chromatography (EtOAc/MeOH=7:3) to afford compound 12.
LC/MS (M$^+$+1): 741.

EXAMPLE 13

Preparation of Compound 13: N-[4-({bis-[2-(4-fluoro-benzylamino)-ethyl]-amino}-methyl)-benzyl]-N'-(4-fluoro-benzyl)-N-[2-(4-fluoro-benzylamino)-ethyl]-ethane-1,2-diamine Compound 13 was prepared in a manner similar to that described in Example 12.
LC/MS (M$^+$+1): 741.

EXAMPLE 14

Preparation of Compound 14: N-{4-[(bis-{2-[(pyridin-2-ylmethyl)-amino]-ethyl}-amino)-methyl]-benzyl}-N'-pyridin-2-ylmethyl-N-{2-[(pyridin-2-ylmethyl)-amino]-ethyl}-ethane-1,2-diamine Compound 14 was prepared in a manner similar to that described in Example 12.
LC/MS (M$^+$+1): 673.

EXAMPLE 15

Preparation of Compound 15: N-(2-amino-ethyl)-N-{4-[((2-amino-ethyl)-{2-[(pyridin-2-ylmethyl)-amino]-ethyl}-amino)-methyl]-benzyl}-N'-pyridin-2-ylmethyl-ethane-1,2-diamine 1,4-Di[bis(2-aminoethyl)amino-methyl]benzene (0.01 mol) and pyridine-2-carbaldehyde (0.02 mol) were dissolved in MeOH (40 mL). After stirring at 25° C. for 15 h, NaBH$_4$ (1.14 g, 0.03 mol) was added to this solution at 0° C. The reaction mixture was stirred for another 2 h at 25° C. It was then diluted with CH$_2$Cl$_2$ (100 mL) and an ammonium chloride aqueous solution (10%, 70 mL). The organic layer was separated, washed with water (100 mL), dried over MgSO$_4$ (s), and concentrated under reduced pressure to yield an oil product. The crude product was purified using alumina column chromatography (EtOAc/MeOH=6:4) to afford compound 15.
LC/MS (M$^+$+1): 491.

EXAMPLE 16

Preparation of Compound 16: N-(4-fluoro-benzyl)-N'-[2-(4-fluoro-benzylamino)-ethyl]-N'-{4-[(4-fluoro-benzylamino)-methyl]-benzyl}-ethane-1,2-diamine Bis(2-tert-butoxycarbonylaminoethyl)amine (0.01 mol), 4-cyanobenzylbromide (0.01 mol), and K$_2$CO$_3$ (0.05 mol) in CH$_3$CN (70 mL) were heated at 60° C. for 10 h. The resultant bis(2-tert-butoxycarbonylaminoethyl)amino-4-methylphenylcyanide was deprotected with HCl/ether and condensed with the 4-fluoro-benzaldehyde (0.02 mol) in MeOH. After sequential treatments with NaBH$_4$, di-tert-butyl dicarbonate, and diisobutylaluminum, bis(2-substituted-aminoethyl) amino-4-methylbenzaldehyde was obtained and further condensed with 4-fluoro-benzylamine to give a Schiff base. The Schiff base was then reduced by NaBH$_4$ and deprotected by

EXAMPLE 17

Preparation of Compound 17: N-{4-[(3-imidazol-1-yl-propylamino)-methyl]-benzyl}-N'-pyridin-2-ylmethyl-N-{2-[(pyridin-2-ylmethyl)-amino]-ethyl}-ethane-1,2-diamine reacting with HCl. A crude product was obtained and purified with alumina column chromatography (EtOAc/MeOH=7:3) to afford compound 16.
LC/MS (M$^+$+1): 747.

EXAMPLE 17

Preparation of Compound 17: N-{4-[(3-imidazol-1-yl-propylamino)-methyl]-benzyl}-N'-pyridin-2-ylmethyl-N-{2-[(pyridin-2-ylmethyl)-amino]-ethyl}-ethane-1,2-diamine Compound 17 was prepared in a manner similar to that described in Example 16.
LC/MS (M$^+$+1): 513.

EXAMPLE 18

Preparation of Compound 18: 1-({4-[(bis-{2-[(pyridin-2-ylmethyl)-amino]-ethyl}-amino)-methyl]-benzylamino}-methyl)-cyclohexanol Compound 18 was prepared in a manner similar to that described in Example 16.
LC/MS (M$^+$+1): 517.

EXAMPLE 19

Preparation of Compound 19: N-{4-[(3-morpholin-4-yl-propylamino)-methyl]-benzyl}-N'-pyridin-2-ylmethyl-N-{2-[(pyridin-2-ylmethyl)-amino]-ethyl}-ethane-1,2-diamine Compound 19 was prepared in a manner similar to that described in Example 16.
LC/MS (M$^+$+1): 532.

EXAMPLE 20

Preparation of Compound 20: N-(4-{[2-(2,5-dimethoxy-phenyl)-ethylamino]methyl}-benzyl)-N'-pyridin-2-ylmethyl-N-{2-[(pyridin-2-ylmethyl)-amino]-ethyl}-ethane-1,2-diamine Compound 20 was prepared in a manner similar to that described in Example 16.
LC/MS (M$^+$+1): 569.

EXAMPLE 21

Preparation of Compound 21: N-(4-{[2-(4-fluoro-phenyl)-1,1-dimethyl-ethylamino]-methyl}-benzyl)-N'-pyridin-2-ylmethyl-N-{2-[(pyridin-2-ylmethyl)-amino]-ethyl}-ethane-1,2-diamine Compound 21 was prepared in a manner similar to that described in Example 16.
LC/MS (M$^+$+1): 555.

EXAMPLE 22

Preparation of Compound 22: N-(4-{[2-(3-fluoro-phenyl)-ethylamino]-methyl}-benzyl)-N'-pyridin-2-ylmethyl-N-{2-[(pyridin-2-ylmethyl)-amino]-ethyl}-ethane-1,2-diamine Compound 21 was prepared in a manner similar to that described in Example 16.
LC/MS (M$^+$+1): 527.

EXAMPLE 23

Preparation of Compound 23: N-(4-{[(1H-benzoimidazol-2-ylmethyl)-amino]-methyl}-benzyl)-N'-pyridin-2-ylmethyl-N-{2-[(pyridin-2-ylmethyl)-amino]-ethyl}-ethane-1,2-diamine Compound 23 was prepared in a manner similar to that described in Example 16.
LC/MS (M$^+$+1): 535.

EXAMPLE 24

Preparation of Compound 24: N-pyridin-2-ylmethyl-N'-{2-[(pyridin-2-ylmethyl)-amino]-ethyl}-N'-(4-{[(pyridin-2-ylmethyl)-amino]-methyl}-benzyl)-ethane-1,2-diamine Compound 24 was prepared in a manner similar to that described in Example 16.
LC/MS (M$^+$+1): 496.

EXAMPLE 25

Preparation of Compound 25: N-(4-{[(pyridin-2-ylmethyl)-amino]-methyl}-benzyl)-N'-(2,3,5-trichloro-benzyl)-N-[2-(2,3,5-trichloro-benzylamino)-ethyl]-ethane-1,2-diamine Compound 25 was prepared in a manner similar to that described in Example 16.
LC/MS (M$^+$+1): 488.

EXAMPLE 26

Preparation of Compound 26: N-(3,4-difluoro-benzyl)-N'-[2-(3,4-difluoro-benzylamino)-ethyl]-N'-(4-{[(pyridin-2-ylmethyl)-amino]-methyl}-benzyl)-ethane-1,2-diamine Compound 26 was prepared in a manner similar to that described in Example 16.
LC/MS (M$^+$+1): 566.

EXAMPLE 27

Preparation of Compound 27: N-(4-fluoro-benzyl)-N'-[2-(4-fluoro-benzylamino)-ethyl]-N'-(4-{[(pyridin-2-ylmethyl)-amino]-methyl}-benzyl)-ethane-1,2-diamine Compound 27 was prepared in a manner similar to that described in Example 16.
LC/MS (M$^+$+1): 530.

EXAMPLE 28

Preparation of Compound 28: N-(4-chloro-benzyl)-N'-[2-(4-chloro-benzylamino)-ethyl]-N'-(4-{[(pyridin-2-ylmethyl)-amino]-methyl}-benzyl)-ethane-1,2-diamine Compound 28 was prepared in a manner similar to that described in Example 16.
LC/MS (M$^+$+1): 563.

EXAMPLE 29

Preparation of Compound 29: N-(4-{[2-(3-chloro-phenyl)-ethylamino]-methyl}-benzyl)-N'-pyridin-2-ylmethyl-N-{2-[(pyridin-2-ylmethyl)-amino]-ethyl}-ethane-1,2-diamine Compound 29 was prepared in a manner similar to that described in Example 16.
LC/MS (M$^+$+1): 543.

EXAMPLE 30

Preparation of Compound 30: N-(4-{[2-(4-chloro-phenyl)-ethylamino]-methyl}-benzyl)-N'-pyridin-2-ylmethyl-N-{2-[(pyridin-2-ylmethyl)-amino]-ethyl}-ethane-1,2-diamine Compound 30 was prepared in a manner similar to that described in Example 16.
LC/MS (M$^+$+1): 543.

EXAMPLE 31

Preparation of Compound 31: N-{4-[(4-fluoro-benzylamino)-methyl]-benzyl}-N'-pyridin-2-ylmethyl-N-{2-[(pyridin-2-ylmethyl)-amino]-ethyl}-ethane-1,2-diamine Compound 31 was prepared in a manner similar to that described in Example 16.
LC/MS (M$^+$+1): 513.

EXAMPLE 32

Preparation of Compound 32: N-(4-{[2-(1H-indol-3-yl)-ethylamino]-methyl}-benzyl)-N'-pyridin-2-ylmethyl-N-{2-[(pyridin-2-ylmethyl)-amino]-ethyl}-ethane-1,2-diamine Compound 32 was prepared in a manner similar to that described in Example 16.
LC/MS (M$^+$+1): 548.

EXAMPLE 33

Preparation of Compound 33: N-(4-{[2-(5-fluoro-1H-indol-3-yl)-ethylamino]-methyl}-benzyl)-N'-pyridin-2-ylmethyl-N-{2-[(pyridin-2-ylmethyl)-amino]-ethyl}-ethane-1,2-diamine Compound 33 was prepared in a manner similar to that described in Example 16.
LC/MS (M$^+$+1): 566.

EXAMPLE 34

Preparation of Compound 34: N-(4-{[2-(5-methoxy-1H-indol-3-yl)-ethylamino]-methyl}-benzyl)-N'-pyridin-2-ylmethyl-N-{2-[(pyridin-2-ylmethyl)-amino]-ethyl}-ethane-1,2-diamine Compound 34 was prepared in a manner similar to that described in Example 16.
LC/MS (M$^+$+1): 578.

EXAMPLE 35

Preparation of Compound 35: N-(4-{[2-(6-methoxy-1H-indol-3-yl)-ethylamino]-methyl}-benzyl)-N'-pyridin-2-ylmethyl-N-{2-[(pyridin-2-ylmethyl)-amino]-ethyl}-ethane-1,2-diamine Compound 35 was prepared in a manner similar to that described in Example 16.
LC/MS (M$^+$+1): 578.

EXAMPLE 36

Preparation of Compound 36: N-(4-{[2-(7-methyl-1H-indol-3-yl)-ethylamino]-methyl}-benzyl)-N'-pyridin-2-ylmethyl-N-{2-[(pyridin-2-ylmethyl)-amino]-ethyl}-ethane-1,2-diamine Compound 36 was prepared in a manner similar to that described in Example 16.
LC/MS (M$^+$+1): 562.

EXAMPLE 37

Preparation of Compound 37: N-{4-[(2-cyclohex-1-enyl-ethylamino)-methyl]-benzyl}-N'-pyridin-2-ylmethyl-N-{2-[(pyridin-2-ylmethyl)-amino]-ethyl}-ethane-1,2-diamine Compound 37 was prepared in a manner similar to that described in Example 16.
LC/MS (M$^+$+1): 513.

EXAMPLE 38

Preparation of Compound 38: N-{4-[(1H-indol-5-ylamino)-methyl]-benzyl}-N'-pyridin-2-ylmethyl-N-{2-[(pyridin-2-ylmethyl)-amino]-ethyl}-ethane-1,2-diamine Compound 38 was prepared in a manner similar to that described in Example 16.
LC/MS (M$^+$+1): 520.

EXAMPLE 39

Preparation of Compound 39: 2-{4-[(bis-{2-[(pyridin-2-ylmethyl)-amino]-ethyl}-amino)-methyl]-benzylamino}-4,5,6,7-tetrahydro-benzo[b]thiophene-3-carboxylic acid ethyl ester Compound 39 was prepared in a manner similar to that described in Example 16.
LC/MS (M$^+$+1): 613.

EXAMPLE 40

Preparation of Compound 40: N-(4-{[2-(4-fluoro-phenyl)-ethylamino]-methyl}-benzyl)-N'-pyridin-2-ylmethyl-N-{2-[(pyridin-2-ylmethyl)-amino]-ethyl}-ethane-1,2-diamine Compound 40 was prepared in a manner similar to that described in Example 16.
LC/MS (M$^+$+1): 527.

EXAMPLE 41

Preparation of Compound 41: N-(4-{[2-(4-chloro-phenyl)-propylamino]-methyl}-benzyl)-N'-pyridin-2-ylmethyl-N-{2-[(pyridin-2-ylmethyl)-amino]-ethyl}-ethane-1,2-diamine Compound 41 was prepared in a manner similar to that described in Example 16.
LC/MS (M$^+$+1): 558.

EXAMPLE 42

Preparation of Compound 42: N-(4-{[2-(5-methyl-1H-indol-3-yl)-ethylamino]-methyl}-benzyl)-N'-pyridin-2-ylmethyl-N-{2-[(pyridin-2-ylmethyl)-amino]-ethyl}-ethane-1,2-diamine Compound 42 was prepared in a manner similar to that described in Example 16.
LC/MS (M$^+$+1): 562.

EXAMPLE 43

Preparation of Compound 43: N-(4-fluoro-benzyl)-N'-[2-(3-fluoro-benzylamino)-ethyl]-N'-(4-{[6-(pyridin-2-yloxy)-pyridin-3-ylamino]-methyl}-benzyl)-ethane-1,2-diamine Compound 43 was prepared in a manner similar to that described in Example 16.
LC/MS (M$^+$+1): 609.

EXAMPLE 44

Preparation of Compound 44: 6-(5-{4-[(bis-{2-[(pyridin-2-ylmethyl)-amino]-ethyl}-amino)-methyl]-benzylamino}-pyridin-2-yloxy)-pyridine-2-carboxylic acid methyl ester Compound 44 was prepared in a manner similar to that described in Example 16.
LC/MS (M$^+$+1): 633.

EXAMPLE 45

Preparation of Compound 45: N-(4-{[6-(5-chloro-pyridin-2-yloxy)-pyridin-3-ylamino]-methyl}-benzyl)-N'-pyridin-2-ylmethyl-N-{2-[(pyridin-2-ylmethyl)-amino]-ethyl}-ethane-1,2-diamine Compound 45 was prepared in a manner similar to that described in Example 16.
LC/MS (M$^+$+1): 609.

EXAMPLE 46

Preparation of Compound 46: N-pyridin-2-ylmethyl-N'-{2-[(pyridin-2-ylmethyl)-amino]-ethyl}-N'-(4-{[6-(pyridin-2-yloxy)-pyridin-3-ylamino]-methyl}-benzyl)-ethane-1,2-diamine Compound 46 was prepared in a manner similar to that described in Example 16.
LC/MS (M$^+$+1): 575.

EXAMPLE 47

Preparation of Compound 47: N-(4-{[(1H-benzoimidazol-2-ylmethyl)-amino]-methyl}-benzyl)-N'-(4-fluoro-benzyl)-N-[2-(4-fluoro-benzylamino)-ethyl]-ethane-1,2-diamine Compound 47 was prepared in a manner similar to that described in Example 16.
LC/MS (M$^+$+1): 569.

EXAMPLE 48

Preparation of Compound 48: 6-{5-[4-({bis-[2-(4-fluoro-benzylamino)-ethyl]-amino}-methyl)-benzylamino]-pyridin-2-yloxy}-pyridine-2-carboxylic acid methyl ester Compound 48 was prepared in a manner similar to that described in Example 16.
LC/MS (M$^+$+1): 667.

EXAMPLE 49

Preparation of Compound 49: N-pyridin-2-ylmethyl-N'-{2-[(pyridin-2-ylmethyl)-amino]-ethyl}-N'-[4-(1,4,8,11tetraaza-cyclotetradec-1-ylmethyl)-benzyl]-ethane-1,2-diamine $K_2CO_3$ (0.05 mol) was added to a solution of tri-Boc-protected cyclam (0.01 mole) and 1,4 dibromomethylbenzene (0.01 mol) in $CH_3CN$ at 60° C. After stirring the reaction mixture for 12 h, tri-Boc-protected bromomethylbenzylcyclam was obtained (0.007 mol). It was then reacted with bis(2-pyridyliminoethyl)amine (0.01 mole) in $CH_3CN$ (100 mL) in the presence of $K_2CO_3$ (0.05 mol) at 60° C. After stirring for 12 h, the reaction mixture was filtered and concentrated. MeOH (50 mL) was added to this mixture, followed by the addition of $NaBH_4$ (0.03 mol) at 25° C. The mixture was stirred for another 2 h. The solution was partitioned between EtOAc and water. The organic layer was then separated, dried over $MgSO_4$ (s), filtered, and concentrated to give a residue. The residue was treated with HCl/ether and purified by alumina column chromatography (EtOAc/MeOH=1:2) to afford compound 49.
LC/MS (M$^+$+1): 588.

EXAMPLE 50

Preparation of Compound 50: 4-[bis-{2-[(pyridin-2-ylmethyl)-amino]-ethyl}-amino)-methyl]-N,N-bis-{2-[(pyridin-2-ylmethyl)-amino]-ethyl}-benzene-sulfonamide 4-Bromomethylbenzenesulfonyl chloride (0.01 mol) was treated with bis(2-tert-butoxycarbonylaminoethyl)amine (0.02 mol) in CH$_3$CN (100 mL) in the presence of K$_2$CO$_3$ (0.1 mol) at 60° C. After stirring for 12 h, the solution was filtered and the filtrate was concentrated to give a residue. The residue was then treated with HCl/ether and neutralized to give a polyamine. This polyamine was treated with the pyridine-2-carbaldehyde to give a Schiff base. The Schiff base was then reduced by NaBH$_4$ in MeOH. The crude product thus obtained was purified by alumina column chromatography (EtOAc/MeOH=1:1) to afford compound 50.

LC/MS (M$^+$+1): 723.

EXAMPLE 51

Preparation of Compound 51: 4-({bis-[2-(3,4-dichloro-benzylamino)-ethyl]-amino}-methyl)-N-pyridin-2-ylmethyl-benzenesulfonamide 4-Bromomethylbenzenesulfonyl chloride (0.01 mol) and 2-aminomethyl pyridine (0.01 mol) were dissolved in ether (100 mL), which contains Et$_3$N (0.02 mol). After stirring for 5 h at 25° C., the solution was washed with water. The resultant bromosulfamide (0.01 mol) was treated with bis(2-tert-butoxycarbonylaminoethyl)amine (0.01 mol) in CH$_3$CN (100 mL) in the presence of K$_2$CO$_3$ (0.05 mol) at 60° C. After stirring for 12 h, the reaction mixture was filtered and the filtrate was concentrated to give a residue. This residue was treated with HCl/ether and neutralized to give a polyamine. The polyamine was then treated with 3,4-dichlorobenzaldehyde to give a Schiff base. The Schiff base was reduced by NaBH$_4$ in MeOH. The crude product thus obtained was purified by alumina column chromatography (EtOAc/MeOH=6:4) to afford compound 51.

LC/MS (M$^+$+1): 680.

EXAMPLE 52

Preparation of Compound 52: 4-({bis-[2-(3,4-difluoro-benzylamino)-ethyl]-amino}-methyl)-N-pyridin-2-ylmethyl-benzenesulfonamide Compound 52 was prepared in a manner similar to that described in Example 51.

LC/MS (M$^+$+1): 616.

EXAMPLE 53

Preparation of Compound 53: 4-({bis-[2-(4-fluoro-benzylamino)-ethyl]-amino}-methyl)-N-pyridin-2-ylmethyl-benzenesulfonamide Compound 53 was prepared in a manner similar to that described in Example 51.

LC/MS (M$^+$+1): 580.

EXAMPLE 54

Preparation of Compound 54: 4-({bis-[2-(4-chloro-benzylamino)-ethyl]-amino}-methyl)-N-pyridin-2-ylmethyl-benzenesulfonamide Compound 54 was prepared in a manner similar to that described in Example 51.

LC/MS (M$^+$+1): 612.

EXAMPLE 55

Preparation of compound 55: 4-({bis-[2-(2-chloro-benzylamino)-ethyl]-amino}-methyl)-N-pyridin-2-ylmethyl-benzenesulfonamide Compound 55 was prepared in a manner similar to that described in Example 51.

LC/MS (M$^+$+1): 612.

EXAMPLE 56

Preparation of Compound 56: N-[4-(6-methoxy-1,3,4,9-tetrahydro-b-carbolin-2-ylmethyl)-benzyl]-N'-pyridin-2-ylmethyl-N-{2-[(pyridin-2-ylmethyl)-amino]-ethyl}-ethane-1,2-diamine 1,4-Dibromoxylene (13.64 mmol) was treated with bis(tert-butoxyaminoethyl)amine (2.74 mmol) in the presence of Et$_3$N (2.74 mmol) in CH$_2$Cl$_2$ (50 mL) at 0° C. After stirring 16 h, the solution was filtered, concentrated, and purified to afford a mono-substituted bromide. This mono-substituted bromide (0.68 mmol) was reacted with 6-methoxy-1,2,3,4-tetrahydro-9H-pyrido[3,4-b]indole (0.68 mmol) in CH$_3$CN (10 mL) in the presence of K$_2$CO$_3$ (3.39 mmol) at 60° C. After stirring for 12 h, the solution was filtered and the filtrate was concentrated and purified by chromatography to give a Boc-protected residue (0.57 mmol; 84% yield). This residue (0.26 mmol) was treated with HCl/ether and neutralized to give a polyamine. This polyamine was then treated with the pyridine-2-carbaldehyde to give a Schiff base. The Schiff base was reduced by NaBH$_4$ in MeOH. The crude product thus obtained was purified by alumina column chromatography (EtOAc/MeOH=7:3) to afford compound 56.

LC/MS (M$^+$+1): 590.

EXAMPLE 57

Preparation of Compound 57: N-pyridin-2-ylmethyl-N'-{2-[(pyridin-2-ylmethyl)-amino]-ethyl}-N'-[4-(1,3,4,9-tetrahydro-b-carbolin-2-ylmethyl)-benzyl]-ethane-1,2-diamine Compound 57 was prepared in a manner similar to that described in Example 56.

LC/MS (M$^+$+1): 560.

EXAMPLE 58

Preparation of Compound 58: isonicotinic acid {4-[(bis-{2-[(pyridin-2-ylmethyl)-amino]-ethyl}-amino)-methyl]-benzylidene}-hydrazide Bis(2-tert-butoxycarbonylaminoethyl)amine (0.01 mol), 4-cyanobenzylbromide (0.01 mol), and K$_2$CO$_3$ (0.05 mol) were added in CH$_3$CN (70 mL) and the mixture were heated at 60° C. while stirring for 10 h. The resultant bis(2-tert-butoxycarbonylaminoethyl)amino-4-methylphenylcyanide was deprotected by treating with HCl/ether and then condensed with pyridine-2-benzaldehyde (0.02 mol) in MeOH. After sequential treatments with NaBH$_4$, di-tert-butyl dicarbonate, and DIBAL, the resultant bis(2-substituted-aminoethyl)amino-4-methylbenzaldehyde was condensed with isonicotinic acid hydrazide to give a Schiff base. The Schiff base was then treated with HCl/ether. The crude product thus obtained was purified by alumina column chromatography (EtOAc/MeOH=7:3) to afford compound 58.
LC/MS (M$^+$+1): 523.

EXAMPLE 59

Preparation of Compound 59: thiophene-2-carboxylic acid {4-[(bis-{2-[(pyridin-2-ylmethyl)-amino]-ethyl}-amino)-methyl]-benzylidene}-hydrazide Compound 59 was prepared in a manner similar to that described in Example 58.
LC/MS (M$^+$+1): 528.

EXAMPLE 60

Preparation of Compound 60: 1-[bis[(2-(2-pyridinylmethyl)aminoethyl)]amino-methyl]-4-[2-(3-indol)-1-((S)-hydroxymethyl)ethylaminomethyl]benzene Compound 60 was prepared in a manner similar to that described in Example 16 (Yield: 80%).
LC-MS ($C_{35}H_{43}N_7O.7HCl$) (M$^+$+1-7HCl): 578.

EXAMPLE 61

Preparation of Compound 61: 1-[bis[(2-(2-pyridinyl-2-ethyl)aminoethyl)]amino-methyl]-4-[2-(3-indol)-1-((S)-hydroxymethyl)ethylaminomethyl]benzene Compound 61was prepared in a manner similar to that described in Example 16 (Yield: 80%).
LC-MS ($C_{35}H_{43}N_7O.7HCl$) (M$^+$+1-7HCl): 606.

EXAMPLE 62

Preparation of Compound 62: 1-[bis[(2-(2-pyridinylmethyl)aminoethyl)]amino-methyl]-4-[2-(phenyl)-1-((R)-hydroxymethyl)ethylaminomethyl]benzene Compound 62 was prepared in a manner similar to that described in Example 16 (Yield: 81%).
LC-MS ($C_{33}H_{42}N_6O.6HCl$) (M$^+$+1-6HCl): 539.

EXAMPLE 63

Preparation of Compound 63: 1-[bis[(2-(2-pyridinylmethyl)aminoethyl)]amino-methyl]-4-[2-(phenyl)-1-((S)-hydroxymethyl)ethylaminomethyl]benzene Compound 63 was prepared in a manner similar to that described in Example 16 (Yield: 85%).
LC-MS ($C_{33}H_{42}N_6O.6HCl$) (M$^+$+1-6HCl): 539.

EXAMPLE 64

Preparation of Compound 64: 1-[bis[(2-(2-pyridinylmethyl)aminoethyl)]amino-methyl]-4-[2-(3-indol)-1-((R)-hydroxymethyl)ethylaminomethyl]benzene Compound 64 was prepared in a manner similar to that described in Example 16 (Yield: 78%).
LC-MS ($C_{35}H_{43}N_7O.7HCl$) (M$^+$+1-7HCl): 578.

EXAMPLE 65

Preparation of Compound 65: 1-[bis[(2-(2-pyridinyl-2-ethyl)aminoethyl)]amino-methyl]-4-[(1,2,3,4-tetrahydro-9H-pyrido-6-methoxy[3,4-b]indol-2-methyl)benzene Compound 65 was prepared by a similar manner to that described in Example 56.
LC/MS (M$^+$+1): 618.

EXAMPLE 66

Preparation of Compound 66: 1-[bis[(2-(2-pyridinylmethyl)aminoethyl)]amino-methyl]-4-[(1,2,3,4-tetrahydro-9H-pyrido-6-benzyloxy[3,4-b]indol-2-methyl)benzene Compound 66 was prepared by a similar manner to that described in Example 56.
LC/MS (M$^+$+1): 666.

EXAMPLE 67

Preparation of Compound 67: 1-[bis[(2-(2-pyridinylmethyl)aminoethyl)]amino-sulfonyl]-4-(1,2,3,4-tetrahydro-9H-pyrido-6-methoxy[3,4-b]indol-2-methyl)benzene Bis(2-tert-butoxycarbonylaminoethyl)amine (3.03 g, 0.01 mol) was added to a solution of 1-bromomethylbenzene-4-sulfonyl chloride (2.68 g, 0.01 mol), $CH_2Cl_2$ (160 mL), and $Et_3N$ (1.01 g, 0.01 mol). The reaction mixture was stirred at 0° C. for 2.5 hours. Then, the solvent was evaporated and the residue was dissolved in a mixture of $CH_3CN$ (180 mL), $K_2CO_3$ (4.14 g, 0.03 mol), and 1,2,3,4-tetrahydro-9H-pyrido-6-methoxy[3,4-b]indole (1.72 g, 0.01 mol). The reaction mixture was stirred at 60° C. for another 10 hours. The mixture was then filtered, concentrated, and treated with a mixture of $CH_2Cl_2$ (35 mL) and HCl/ether (1.0 M, 80 mL) for 12 hours. The reaction mixture was subsequently concentrated, stirred with anhydrous $K_2CO_3$ (10.0 g, 30 min) in $CH_2Cl_2$ (150 mL). The mixture thus obtained was filtered and concentrated to afford intermediate 1, 1-[bis[(2-aminoethyl)]aminosulfonyl]-4-[(1,2,3,4-tetrahydro-9H-pyrido-6-methoxy[3,4-b]indol-2-methyl)benzene (2.56 g, 0.006 mol) in 60% yield. This intermediate was then treated with pyridine-2-carboxaldehyde (1.50 g, 0.014 mol) in MeOH (40 mL) for 14 hours and then with NaBH$_4$ (1.60 g, 0.042 mol) for 4 hours to give a crude intermediate 2. Intermediate 2 was purified using alumina column chromatography (EtOAc/MeOH=7:3) (3.19 g, 0.005 mol, 83% yield). Intermediate 2 was subsequently treated with HCl/ether (125 mL) in $CH_2Cl_2$ (50 mL) to afford compound 67.
LC-MS ($C_{35}H_{41}N_7O_3S.6HCl$) (M$^+$+1-6HCl): 640.

EXAMPLE 68

Preparation of Compound 68: N-[4-(6-methoxy-1,3,4,9-tetrahydro-b-carbolin-2-ylmethyl)-benzyl]-N'-pyridin-2-ylmethyl-N-{2-[(pyridin-2-ylmethyl)-2-hydroxyethylamino]-ethyl}-ethane-1,2-diamine Compound 68 was prepared by selective alkylation of compound 56 (Yield: 40%).
LC-MS ($C_{38}H_{47}N_7O_2.7HCl$) (M$^+$+1-7HCl): 634.

EXAMPLE 69

Preparation of Compound 69: 1-[bis[(2-(2-pyridinyl-methyl)aminoethyl)]amino-methyl]-4-[2-(phenyl)-1-((R)-hydroxycarbonyl)ethylaminomethyl]benzene Compound 69 was prepared in a manner similar to that described in Example 16 (Yield: 70%).
LC-MS ($C_{33}H_{40}N_6O_2 \cdot 6HCl$) ($M^+ + 1 - 6HCl$): 553.

EXAMPLE 70

Preparation of Compound 70: 1-[bis[(2-(2-pyridinyl-methyl)aminoethyl)]amino-methyl]-4-[2-(3-(5-hydroxyindol)-1-((R)-hydroxycarbonyl)ethylaminomethyl]benzene Compound 70 was prepared in a manner similar to that described in Example 16 (Yield: 75%).
LC-MS ($C_{35}H_{41}N_7O_3 \cdot 7HCl$) ($M^+ + 1 - 7HCl$): 608.

EXAMPLE 71

Preparation of Compound 71: 1-[bis[(2-(2-pyridinyl-methyl)aminoethyl)]amino-methyl]-4-[2-(3-(7-methylindol))ethylaminomethyl]benzene Compound 71 was prepared in a manner similar to that described in Example 16 (Yield: 70%).
LC-MS ($C_{37}H_{47}N_7 \cdot 7HCl$) ($M^+ + 1 - 7HCl$): 590.

EXAMPLE 72

Preparation of Compound 72: 1-[bis[(2-(2-pyridinyl-2-ethyl)aminoethyl)]amino-methyl]-4-[2-(3-chlorophenyl)ethylaminomethyl]benzene Compound 72 was prepared in a manner similar to that described in Example 16 (Yield: 80%).
LC-MS ($C_{34}H_{43}ClN_6 \cdot 6HCl$) ($M^+ + 1 - 6HCl$): 571.

EXAMPLE 73

Preparation of Compound 73: 1-[bis[(2-(2-pyridinyl-2-ethyl)aminoethyl)]amino-methyl]-4-{[(1H-benzoimidazol-2-ylmethyl)-amino]-methyl}benzene Compound 73 was prepared in a manner similar to that described in Example 16 (Yield: 84%).
LC-MS ($C_{34}H_{42}N_8 \cdot 7HCl$) ($M^+ + 1 - 6HCl$): 563.

EXAMPLE 74

Preparation of Compound 74: 1-[bis[(2-(2-pyridinyl-methyl)aminoethyl)]amino-methyl]-4-[(2-phenyl-2-hydroxy-1-methoxymethyl)ethylaminomethyl]benzene Compound 74 was prepared in a manner similar to that described in Example 16 (Yield: 71%).
LC-MS ($C_{34}H_{44}N_6O_2 \cdot 6HCl$) ($M^+ + 1 - 6HCl$): 569.

EXAMPLE 75

Preparation of Compound 75: 1-[bis[(2-(2-pyridinyl-methyl)aminoethyl)]amino-methyl]-4-[(2-(4-chlorophenyl)-1-hydroxymethyl)ethylaminomethyl]benzene Compound 75 was prepared in a manner similar to that described in Example 16 (Yield: 70%).
LC-MS ($C_{33}H_{41}ClN_6O \cdot 6HCl$) ($M^+ + 1 - 6HCl$): 573.

EXAMPLE 76

Preparation of Compound 76: 1-[bis[(2-(2-pyridinyl-methyl)aminoethyl)]amino-methyl]-4-[(2-phenyl-(2R)-hydroxy-(1R)-hydroxymethyl)ethylaminomethyl]benzene Compound 76 was prepared in a manner similar to that described in Example 16 (Yield: 68%).
LC-MS ($C_{33}H_{42}N_6O_2 \cdot 6HCl$) ($M^+ + 1 - 6HCl$): 555.

EXAMPLE 77

Preparation of Compound 77: 1-[bis[(2-(2-pyridinyl-methyl)aminoethyl)]amino-methyl]-4-[(2-phenyl-(2S)-hydroxy-(1S)-hydroxymethyl)ethylaminomethyl]benzene Compound 77 was prepared in a manner similar to that described in Example 16 (Yield: 70%).
LC-MS ($C_{33}H_{42}N_6O_2 \cdot 6HCl$) ($M^+ + 1 - 6HCl$): 555.

EXAMPLE 78

Preparation of Compound 78: 1-[bis[(2-(2-pyridinyl-methyl)aminoethyl)]amino-methyl]-4-[2-(4-bromophenyl)-1-((R)-hydroxycarbonyl)ethylaminomethyl]benzene Compound 78 was prepared in a manner similar to that described in Example 16 (Yield: 77%).
LC-MS ($C_{33}H_{39}BrN_6O_2 \cdot 6HCl$) ($M^+ + 1 - 6HCl$): 631.

EXAMPLE 79

Preparation of Compound 79: 2-({4'-[(bis-{2-[(pyridin-2-ylmethyl)-amino]-ethyl}-amino)-methyl]-biphenyl-4-ylmethyl}-pyridin-2-ylmethyl-amino)-3-phenyl-propan-1-ol Compound 79 was prepared in a manner similar to that described in Example 16 (Yield: 70%).
LC-MS ($C_{45}H_{51}N_7O \cdot 7HCl$) ($M^+ + 1 - 7HCl$): 706.

EXAMPLE 80

Preparation of Compound 80: N-pyridin-2-ylmethyl-N'-{2-[(pyridin-2-ylmethyl)-amino]-ethyl}-N'-[4-(6-chloro-1,3,4,9-tetrahydro-b-carbolin-2-ylmethyl)-benzyl]-ethane-1,2-diamine Compound 80 was prepared in a manner similar to that described in Example 56.
LC-MS ($C_{35}H_{40}ClN_7 \cdot 7HCl$) ($M^+ + 1 - 7HCl$): 594.

EXAMPLE 81

Preparation of Compound 81: N-[4-({ethyl-[2-(7-methyl-1H-indol-3-yl)-ethyl]-amino}-methyl)-benzyl]-N'-pyridin-2-ylmethyl-N-{2-[(pyridin-2-ylmethyl)-amino]-ethyl}-ethane-1,2-diamine Compound 81 was prepared in a manner similar to that described in Example 56.
LC-MS ($C_{37}H_{47}N_7$.7HCl) ($M^+$+1-7HCl): 590.

EXAMPLE 82

Preparation of Compound 82: N-[4-({[2-(3-chlorophenyl)-ethyl]-ethyl-amino}-methyl)-benzyl]-N'-pyridin-2-ylmethyl-N-{2-[(pyridin-2-ylmethyl)-amino]-ethyl}-ethane-1,2-diamine Compound 82 was prepared in a manner similar to that described in Example 56.
LC-MS ($C_{34}H_{43}ClN_6$.6HCl) ($M^+$+1-6HCl): 571.

EXAMPLE 83

Preparation of Compound 83: 1-[bis[(2-(2-pyridinylmethyl)aminoethyl)]amino-methyl]-4-[(2S)-hydroxymethylpyrrolidine-N-methyl]benzene Compound 83 was prepared in a manner similar to that described in Example 56 (Yield: 80%).
LC-MS ($C_{29}H_{40}N_6O$.6HCl) ($M^+$+1-6HCl): 489.

EXAMPLE 84

Preparation of Compound 84: 1-[bis[(2-(2-pyridinylmethyl)aminoethyl)]amino-methyl]-4-[(2R)-hydroxymethylpyrrolidine-N-methyl]benzene Compound 84 was prepared in a manner similar to that described in Example 56 (Yield: 80%).
LC-MS ($C_{29}H_{40}N_6O$.6HCl) ($M^+$+1-6HCl): 489.

EXAMPLE 85

Preparation of Compound 85: 2-({4'-[(bis-{2-[(pyridin-2-ylmethyl)-amino]-ethyl}-amino)-methyl]-biphenyl-4-ylmethyl}-amino)-3-phenyl-propan-1-ol Compound 85 was prepared in a manner similar to that described in Example 16.
LC-MS ($C_{39}H_{46}N_6O$.6HCl) ($M^+$+1-6HCl): 615.

EXAMPLE 86

Preparation of Compound 86: N-pyridin-2-ylmethyl-N'-{2-[(pyridin-2-ylmethyl)-amino]-ethyl}-N'-[4-(6-fluoro-1,3,4,9-tetrahydro-b-carbolin-2-ylmethyl)-benzyl]-ethane-1,2-diamine Compound 86 was prepared in a manner similar to that described in Example 56.
LC-MS ($C_{35}H_{40}FN_7$.7HCl) ($M^+$+1-7HCl): 578.

EXAMPLE 87

Preparation of Compound 87: 1-[bis[(2-(2-pyridinylmethyl)aminoethyl)]amino-methyl]-4-[2-(5-chloro-6-hydroxyphenyl-1-hydroxycarbonyl)ethylaminomethyl]benzene Compound 87 was prepared in a manner similar to that described in Example 16 (Yield: 76%).
LC-MS ($C_{33}H_{39}ClN_6O_3$.6HCl) ($M^+$+1-6HCl): 603.

EXAMPLE 88

Preparation of Compound 88: 1-[bis[(2-(2-pyridinylmethyl)aminoethyl)]amino-methyl]-4-[(2-thiophene-1-hydroxycarbonyl)ethylaminomethyl]benzene Compound 88 was prepared in a manner similar to that described in Example 16 (Yield: 70%).
LC-MS ($C_{31}H_{38}ClN_6O_2S$.6HCl) ($M^+$+1-6HCl): 559.

EXAMPLE 89

Preparation of Compound 89: 1-[bis[(2-(2-pyridinylmethyl)aminoethyl)]amino-methyl]-4-{[2-(4-chlorophenyl)-2-cyclopropyl]ethylaminomethyl}benzene Compound 89 was prepared in a manner similar to that described in Example 16 (Yield: 78%).
LC-MS ($C_{34}H_{41}ClN_6$.6HCl) ($M^+$+1-6HCl): 569.

EXAMPLE 90

Preparation of Compound 90: 1-[bis[(2-(2-pyridinylmethyl)aminoethyl)]amino-methyl]-4-{[2-(3-chloro-6-methoxyphenyl)]ethylaminomethyl}benzene Compound 90 was prepared in a manner similar to that described in Example 16 (Yield: 80%).
LC-MS ($C_{33}H_{41}ClN_6O$.6HCl) ($M^+$+1-6HCl): 573.

EXAMPLE 91

Preparation of Compound 91: N-pyridin-2-yl-2-ethyl-N'-{2-[(pyridin-2-ylmethyl)-amino]-ethyl}-N'-[4-(6-methoxy-1,3,4,9-tetrahydro-b-carbolin-2-ylmethyl)-benzyl]-ethane-1,2-diamine Compound 91 was prepared in a manner similar to that described in Example 56 (Yield: 65%).
LC-MS ($C_{37}H_{45}N_7O$.7HCl) ($M^+$+1-7HCl): 604.

EXAMPLE 92

Preparation of Compound 92: 1-[bis[(2-(2-pyridinylmethyl)aminoethyl)]amino-methyl]-4-[(2-thiophene-2-hydroxycarbonyl)ethylaminomethyl]benzene Compound 92 was prepared in a manner similar to that described in Example 16 (Yield: 85%).
LC-MS ($C_{31}H_{38}N_6O_2S$.6HCl) ($M^+$+1-6HCl): 559.

EXAMPLE 93

Preparation of Compound 93: 1-[bis[(2-(2-pyridinyl-methyl)aminoethyl)]amino-methyl]-4-[3-hydroxymethyl-(S)-1,2,3,4-tetrahydroisoquinoline-N-ylmethyl]benzene Compound 93 was prepared in a manner similar to that described in Example 56.
LC-MS ($C_{34}H_{42}N_6O.6HCl$) ($M^++1$-6HCl): 551.

EXAMPLE 94

Preparation of Compound 94: 1-[bis[(2-(2-pyridinyl-methyl)aminoethyl)]amino-methyl]-4-(4-hydroxy-4-phenylpiperidine-N-ylmethyl)benzene Compound 94 was prepared in a manner similar to that described in Example 56.
LC-MS ($C_{35}H_{44}N_6O.6HCl$) ($M^++1$-6HCl): 565.

EXAMPLE 95

Preparation of Compound 95: 1-[bis[(2-(2-pyridinyl-methyl)aminoethyl)]amino-methyl]-4-[4-hydroxy-4-(4-chlorophenylpiperidine)-N-ylmethyl]benzene Compound 95 was prepared in a manner similar to that described in Example 56.
LC-MS ($C_{35}H_{43}ClN_6O.6HCl$) ($M^++1$-6HCl): 599.

EXAMPLE 96

Preparation of Compound 96: 1-[bis[(2-(2-pyridinyl-methyl)aminoethyl)]amino-methyl]-4-(1-indanaminomethyl)benzene Compound 96 was prepared in a manner similar to that described in Example 16.
LC-MS ($C_{33}H_{40}N_6.6HCl$) ($M^++1$-6HCl): 521.

EXAMPLE 97

Preparation of Compound 97: 1-[bis[(2-(2-pyridinyl-methyl)aminoethyl)]amino-methyl]-4-(3,4-dichlorophenylmethylaminomethyl)benzene Compound 97 was prepared in a manner similar to that described in Example 16.
LC-MS ($C_{31}H_{36}Cl_2N_6.6HCl$) ($M^++1$-6HCl): 563.

EXAMPLE 98

Preparation of Compound 98: 1-[bis[(2-(2-pyridinyl-methyl)aminoethyl)]amino-methyl]-4-(3-chlorophenylmethylaminomethyl)benzene Compound 98 was prepared in a manner similar to that described in Example 16.
LC-MS ($C_{31}H_{37}ClN_6.6HCl$) ($M^++1$-6HCl): 529.

EXAMPLE 99

Preparation of Compound 99: 1-[bis[(2-(2-pyridinyl-methyl)aminoethyl)]amino-methyl]-4-[4-hydroxyphenyl(1-hydroxymethyl)ethylaminomethyl)benzene Compound 99 was prepared in a manner similar to that described in Example 16.
LC-MS ($C_{33}H_{42}N_6O_2.6HCl$) ($M^++1$-6HCl): 555.

EXAMPLE 100

Preparation of Compound 100: N-(4-{[2-(7-methyl-1H-indol-3-yl)-1-(hydroxycarbonylmethyl)ethylamino]-methyl}-benzyl)-N'-pyridin-2-ylmethyl-N-{2-[(pyridin-2-ylmethyl)-amino]-ethyl}-ethane-1,2-diamine Compound 100 was prepared in a manner similar to that described in Example 16.
LC-MS ($C_{37}H_{45}N_7O_2.6HCl$) ($M^++1$-6HCl): 620.

EXAMPLE 101

Preparation of Compound 101: N-(4-{[2-(7-methyl-1H-indol-3-yl)-1-(hydroxyethyl)ethylamino]-methyl}-benzyl)-N'-pyridin-2-ylmethyl-N-{2-[(pyridin-2-ylmethyl)-amino]-ethyl}-ethane-1,2-diamine Compound 101 was prepared in a manner similar to that described in Example 16.
LC-MS ($C_{37}H_{47}N_7O.7HCl$) ($M^++1$-7HCl): 606.

EXAMPLE 102

Preparation of Compound 102: 1-[bis[(2-(2-pyridinylmethyl)aminoethyl)]amino-methyl]-4-{[2-(3-chloro-4-ethylphenyl)]ethylaminomethyl}benzene Compound 102 was prepared in a manner similar to that described in Example 16 (Yield: 80%).
LC-MS ($C_{33}H_{41}ClN_6O.6HCl$) ($M^++1$-6HCl): 573.

EXAMPLE 103

Preparation of Compound 103: N-(4-{[2-(7-methyl-1H-indol-3-yl)ethylamino]-methyl}-benzyl)-N'-pyridin-2-ylmethyl-N-{2-[(pyridin-2-ylmethyl)-amino]-ethyl}-propane-1,3-diamine Compound 103 was prepared in a manner similar to that described in Example 16.
LC-MS ($C_{36}H_{45}N_7.7HCl$) ($M^++1$-7HCl): 576.

EXAMPLE 104

Preparation of Compound 104: N-(4-{[2-(3-chlorophenyl)ethylamino]methyl}-benzyl)-N'-pyridin-2-ylmethyl-N-{2-[(pyridin-2-ylmethyl)-amino]-ethyl}-propane-1,3-diamine Compound 104 was prepared in a manner similar to that described in Example 16.
LC-MS ($C_{33}H_{41}ClN_6.6HCl$) ($M^++1$-6HCl): 557.

EXAMPLE 105

Preparation of Compound 105: N-(4-{[(1H-benzoimidazol-2-yl-methyl)amino]-methyl}-benzyl)-N'-pyridin-2-ylmethyl-N-{2-[(pyridin-2-ylmethyl)-amino]-ethyl}-propane-1,3-diamine Compound 105 was prepared in a manner similar to that described in Example 16.
LC-MS ($C_{33}H_{40}N_8$.7HCl) ($M^+$+1-7HCl): 549.

EXAMPLE 106

Preparation of Compound 106: N-pyridin-2-yl-hydroxyethyl-N'-{2-[(pyridin-2-ylmethyl)-amino]-ethyl}-N'-[4-(6-methoxy-1,3,4,9-tetrahydro-b-carbolin-2-ylmethyl)-benzyl]-ethane-1,2-diamine Compound 106 was prepared in a manner similar to that described in Example 56 (Yield: 65%).
LC-MS ($C_{37}H_{45}N_7O_2$.7HCl) ($M^+$+1-7HCl): 620.

EXAMPLE 107

Preparation of Compound 107: 1-[bis[(2-(2-pyridinylmethyl)aminoethyl)]amino-methyl]-4-(2-methoxymethylpyrrolidine-N-methylbenzene Compound 107 was prepared in a manner similar to that described in Example 56 (Yield: 82%).
LC-MS ($C_{30}H_{42}N_6O$.6HCl) ($M^+$+1-6HCl): 503.

EXAMPLE 108

Preparation of Compound 108: N-pyridin-2-yl-hydroxyethyl-N'-{2-[(pyridin-2-ylmethyl)-amino]-ethyl}-N'-[4-(1-hydroxymethyl-6-methoxy-1,3,4,9-tetrahydro-b-carbolin-2-yl-methyl)-benzyl]-ethane-1,2-diamine Compound 108 was prepared in a manner similar to that described in Example 56.
LC-MS ($C_{37}H_{45}N_7O_2$.7HCl) ($M^+$+1-7HCl): 620.

EXAMPLE 109

Preparation of Compound 109: N-pyridin-2-yl-hydroxyethyl-N'-{2-[(pyridin-2-ylmethyl)-amino]-ethyl}-N'-[4-(4-phenyl-1,2,3,6-tetrahydropyridine-1-methyl)-benzyl]-ethane-1,2-diamine Compound 109 was prepared in a manner similar to that described in Example 56.
LC-MS ($C_{35}H_{42}N_6$.6HCl) ($M^+$+1-6HCl): 547.

EXAMPLE 110

Preparation of Compound 110: N-pyridin-2-yl-2-ethyl-N'-{2-[(pyridin-2-yl-ethyl)-amino]-ethyl}-4-(cyanobenzyl]-ethane-1,2-diamine.5HCl A mixture of bis(2-tert-butoxycarbonylaminoethyl)amine (0.01 mol), 4-cyanobenzyl-bromide (0.01 mol), $K_2CO_3$ (0.05 mol), and $CH_3CN$ (70 mL) was heated at 60° C. for 10 hours. The resultant bis(2-tert-butoxycarbonylaminoethyl)amino-4-methylphenylcyanide was deprotected using HCl/ether, condensed with 2-acetyl pyridine (0.01 mol) in MeOH, and then reduced by $NaBH_4$. After sequential treatments with pyridine-2-carboxaldehyde, $NaBH_4$, and HCl, compound 110 was obtained in 75% overall yield.
LC-MS ($C_{25}H_{30}N_6$.5HCl) ($M^+$+1-5HCl): 415.

EXAMPLE 111

Preparation of Compound 111: N-pyridin-2-yl-2-ethyl-N'-{2-[(pyridin-2-ylmethyl)-amino]-ethyl}-N'-[4-(1H-benzimidazol-2-yl-methyl)-aminomethyl] benzyl]-ethane-1,2-diamine A mixture of bis(2-tert-butoxycarbonylaminoethyl)amine (0.01 mol), 4-cyanobenzyl-bromide (0.01 mol), $K_2CO_3$ (0.05 mol), and $CH_3CN$ (70 mL) was heated at 60° C. for 10 hours. The resultant bis(2-tert-butoxycarbonylaminoethyl)amino-4-methylphenylcyanide was deprotected by HCl/ether, condensed with 2-acetyl pyridine (0.01 mol) in MeOH, and then reduced by $NaBH_4$. After sequential treatments with pyridine-2-carboxaldehyde, $NaBH_4$, di-tert-butyl dicarbonate, and diisobutylaluminum, the aldehyde thus obtained was condensed with 2-aminomethylbenzimidazole to give a Schiff base. The Schiff base was then reduced by $NaBH_4$ and deprotected by HCl to afford compound 111 in 45% overall yield.
LC-MS ($C_{33}H_{40}N_8$.7HCl) ($M^+$+1-7HCl): 549.

EXAMPLE 112

Preparation of Compound 112: 1-[bis[(2-(2-pyridinylmethyl)aminoethyl)]amino-methyl]-4-[4-hydroxy-4-(4-methoxyphenylpiperidine)-N-yl-methyl] benzene Compound 112 was prepared in a manner similar to that described in Example 67.
LC-MS ($C_{36}H_{46}N_6O_2$.6HCl) ($M^+$+1-6HCl): 595.

EXAMPLE 113

Preparation of Compound 113: 1-[bis[(2-(2-pyridinylmethyl)aminoethyl)]amino-methyl]-4-[4-hydroxy-4-(2-methoxyphenylpiperidine)-N-yl-methyl] benzene Compound 113 was prepared in a manner similar to that described in Example 56.
LC-MS ($C_{36}H_{46}N_6O_2$.6HCl) ($M^+$+1-6HCl): 595.

EXAMPLE 114

Preparation of Compound 114: N-(4-{[2-(7-methyl-1H-indol-3-yl)ethylamino]-methyl}-benzyl)-N'-pyridin-2-ylmethyl-N-{2-[(pyridin-2-ylmethyl)-amino]-ethyl}-1-methylethane-1,2-diamine 4-Cyanobenzaldehyde (0.01 mol) was treated with 2-methyl-2-aminoethanol (0.01 mol) in MeOH (20 mL) at 60° C. for 12 hours. $NaBH_4$ (1.90 g, 0.05 mol) was then added to the above solution at 0° C. The reaction mixture was stirred for another 2 hours at 25° C. It was then diluted with $CH_2Cl_2$ (100 mL) and with an ammonium chloride aqueous solution (10%, 70 mL). The organic layer was separated, washed with water (100 mL), dried over $MgSO_4$ (s), and concentrated under reduced pressure to yield an oil intermediate. The oil intermediate was then condensed with 2-(2-bromo-ethoxy)-tetrahydro-pyran (0.01 mol) in the presence of $K_2CO_3$ (0.05 mol) in refluxing CH$_3$CN (30 mL). After deprotection, the resultant hydroxyl group was mesylated and was allowed to react with 2-aminomethylpyridine. The resultant secondary amine was then protected with the Boc group. Subsequently, the cyanide group was treated with diisobutylaluminum and the aldehyde thus obtained was sequentially treated with 6-methyl-3-aminoethylindol, NaBH$_4$, triflic acid, and HCl to afford compound 114 in 60% overall yield.

LC-MS (C$_{36}$H$_{45}$N$_7$.6HCl) (M$^+$+1-6HCl): 576.

EXAMPLE 115

Preparation of Compound 115: 2-{4-[(bis-{2-[(pyridin-2-ylmethyl)-amino]-ethyl}-amino)-methyl]-benzylamino}-1-(3-chloro-phenyl)-ethanol Compound 115 was prepared in a manner similar to that described in Example 16 (Yield: 77%).
LC-MS (M$^+$+1): 559.

EXAMPLE 116

Preparation of Compound 116: N-(4-{[(1H-benzoimidazol-2-ylmethyl)-amino]-methyl}-benzyl)-N'-piperidin-4-yl-N-{2-[(pyridin-2-ylmethyl)-amino]-ethyl}-ethane-1,2-diamine Compound 116 was prepared in a manner similar to that described in Example 111 (Yield: 70%).
LC-MS (M$^+$+1): 527.

EXAMPLE 117

Preparation of Compound 117: N-(4-{[2-(7-methyl-1H-indol-3-yl)-ethylamino]-methyl}-benzyl)-N'-(1-pyridin-2-yl-ethyl)-N-{2-[(pyridin-2-ylmethyl)-amino]-ethyl}-ethane-1,2-diamine Compound 117 was prepared in a manner similar to that described in Example 111 (Yield: 70%).
LC-MS (M$^+$+1): 576.

EXAMPLE 118

Preparation of Compound 118: N2-(4-{[(1H-benzoimidazol-2-ylmethyl)-amino]-methyl}-benzyl)-N1-pyridin-2-ylmethyl-N2-{2-[(pyridin-2-ylmethyl)-amino]-ethyl}-propane-1,2-diamine Compound 118 was prepared in a manner similar to that described in Example 114 (Yield: 68%).
LC-MS (M$^+$+1): 549.

EXAMPLE 119

Preparation of Compound 119: N2-(4-{[2-(3-chloro-phenyl)-ethylamino]-methyl}-benzyl)-N1-pyridin-2-ylmethyl-N2-{2-[(pyridin-2-ylmethyl)-amino]-ethyl}-propane-1,2-diamine Compound 119 was prepared in a manner similar to that described in Example 114 (Yield: 69%).
LC-MS (M$^+$+1): 557.

EXAMPLE 120

Preparation of Compound 120: N-ethyl-N'-(4-{[2-(7-methyl-1H-indol-3-yl)-ethylamino]-methyl}-benzyl)-N-pyridin-2-ylmethyl-N'-{2-[(pyridin-2-ylmethyl)-amino]-ethyl}-ethane-1,2-diamine Compound 120 was prepared in a manner similar to that described in Example 111 followed by reaction with acetaldehyde and NaBH$_4$ (Yield: 75%).
LC-MS (M$^+$+1): 590.

EXAMPLE 121

Preparation of Compound 121: 3-{4-[(bis-{2-[(pyridin-2-ylmethyl)-amino]-ethyl}-amino)-methyl]-benzylamino}-1-(3-chloro-phenyl)-propan-1-ol Compound 121 was prepared in a manner similar to that described in Example 16 (Yield: 70%).
LC-MS (M$^+$+1): 573.

EXAMPLE 122

Preparation of Compound 122: 1-(3-benzyloxy-phenyl)-3-{4-[(bis-{2-[(pyridin-2-ylmethyl)-amino]-ethyl}-amino)-methyl]-benzylamino}-propan-1-ol Compound 122 was prepared in a manner similar to that described in Example 16 (Yield: 67%).
LC-MS (M$^+$+1): 645.

EXAMPLE 123

Preparation of Compound 123: 3-[2-((4-{[2-(7-methyl-1H-indol-3-yl)-ethylamino]-methyl}-benzyl)-{2-[(pyridin-2-ylmethyl)-amino]-ethyl}-amino)-ethylamino]-3-pyridin-2-yl-propan-1-ol Compound 123 was prepared in a manner similar to that described in Example 111 (Yield: 73%).
LC-MS (M$^+$+1): 606.

EXAMPLE 124

Preparation of Compound 124: 3-[2-((4-{[(1H-benzoimidazol-2-ylmethyl)-amino]-methyl}-benzyl)-{2-[(pyridin-2-ylmethyl)-amino]-ethyl}-amino)-ethylamino]-3-pyridin-2-yl-propan-1-ol Compound 124 was prepared in a manner similar to that described in Example 111 (Yield: 60%).
LC-MS (M$^+$+1): 579.

EXAMPLE 125

Preparation of Compound 125: N-(4-{[(1H-benzoimidazol-2-ylmethyl)-amino]-methyl}-benzyl)-N'-pyridin-2-ylmethyl-N-{2[(pyridin-2-ylmethyl)-amino]-ethyl}-ethane-1,2-diamine Compound 125 was prepared in a manner similar to that described in Example 16 (Yield: 70%).
LC-MS (M$^+$+1): 535.

EXAMPLE 126

Preparation of Compound 126: N-(4-{[3-(3-chloro-phenyl)-propylamino]-methyl}-benzyl)-N'-pyridin-2-ylmethyl-N-{2-[(pyridin-2-ylmethyl)-amino]-ethyl}-ethane-1,2-diamine Compound 126 was prepared in a manner similar to that described in Example 16 (Yield: 85%).
LC-MS ($M^{+}+1$): 557.

EXAMPLE 127 in vitro Assay

Compounds 1-126 were tested for their efficacy in binding to CXCR4 receptor using a DELFIA GTP-binding kit (Wallac Oy, Turku, Finland). The DELFIA GTP-binding assay is a time-resolved fluorometric assay based on GDP-GTP exchange on G-protein subunits followed by activation of a G protein-coupled receptor by its agonists. Eu-GTP, obtained from Wallac Oy, was used in this assay to allow monitoring of agonist-dependent activation of G-protein. Stimulation of CXCR4 receptor by SDF-1 leads to the replacement of GDP by GTP on the α-subunit of G-protein. This GTP-Gα complex represents the activated form of G-protein. Eu-GTP, a non-hydrolysable analog of GTP, can be used to quantify the amount of activated G-protein. (Peltonen et al., Eur. J. Pharmacol. (1998) 355:275.)

Plasma membrane of CXCR4-expressing HEK293 cells was suspended in an assay buffer (50 mM NaCl, 100 µg/mL saponin, 3 mM $MgCl_2$, 3 µM GDP, 5% BSA, 50 mM HEPES, pH 7.4). An aliquot (4 µg protein) was added to each well of an AcroPlate (Pall Life Sciences, Ann Arbor, Mich.). After the addition of the test compounds (10 µM in 0.1% DMSO) and stromal-derived factor-1 (4 nM in the assay buffer), the assay plate was incubated in the dark at room temperature with slow shaking for 10 minutes. Eu-GTP was added to each well and the plate was incubated again for 60 minutes. The assay was terminated by washing the plate twice with a wash solution provided in the assay kit. Binding of Eu-GTP was determined based on the fluorescence signal from a Victor 2 multi-label reader.

Unexpectedly, all of the tested compounds showed $IC_{50}$ values lower than 10 µM. Specifically, 97 of the test compounds showed $IC_{50}$ values lower than 1 µM. Among them, 56 showed $IC_{50}$ values between 0.004 µM and 0.1 µM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

For example, the polyamine compounds described above can be used to treat an inflammatory or immune disease through mechanisms other than binding to CXCR4 receptor. Further, other uses of these compounds are also within the scope of this invention.

What is claimed is:

1. A compound of the formula:

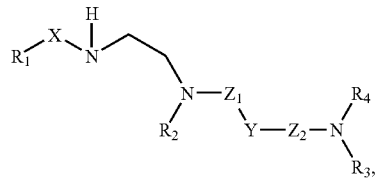

wherein

X is $-CH_2-$, $-C_2H_4-$, or $-C_3H_6-$;

Y is aryl, heteroaryl, $C_3$-$C_8$ cycloalkyl, $C_5$-$C_8$ cycloalkenyl, $C_3$-$C_8$ heterocycloalkyl, or $C_5$-$C_8$ heterocycloalkenyl;

each of $Z_1$ and $Z_2$, independently, is $-CH_2-$, $-C_2H_4-$, or $-C_3H_6-$;

$R_1$ is aryl or heteroaryl;

$R_2$ is $-A_1$-$B_1$-$D_1$-$E_1$;

$R_3$ is $-A_2$-$B_2$-$D_2$-$E_2$; and $R_4$ is $-A_3$-$B_3$-$D_3$-$E_3$ or, together with $R_3$, is $C_4$-$C_{20}$ heterocycloalkyl;

in which $A_1$ is $-CH_2-$, $-C_2H_4-$, $-C_3H_6-$, $-C_4H_8-$, or $-C_5H_{10}-$ $B_1$ is $-NR-$; $D_1$ is $-CH_2-$, $-C_2H_4-$, or $-C_3H_6-$; and $E_1$ is aryl or heteroaryl;

$A_2$ deleted; $B_2$ is deleted; $D_2$ is deleted; and $E_2$ is H, $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl;

$A_3$ is $-CH_2-$, $-C_2H_4-$, $-C_3H_6-$, $-C_4H_8-$, $-C_5H_{10}-$, or deleted; $B_3$ is deleted; $D_3$ is deleted; and $E_3$ is $C_3$-$C_8$ cycloalkyl, $C_5$-$C_8$ cycloalkenyl, $C_3$-$C_8$ heterocycloalkyl, $C_5$-$C_8$ heterocycloalkenyl, aryl, or heteroaryl; and each R, independently, being H or $C_1$-$C_{10}$ alkyl.

2. The compound of claim 1, wherein X is $-CH_2-$ or $-CH(CH_3)-$, Y is phenyl, $Z_1$ is $-CH_2-$, and $Z_2$ is $-CH_2-$.

3. The compound of claim 2, wherein $R_3$ is $-A_2$-$B_2$-$D_2$-$E_2$ or, together with $R_4$, is $C_4$-$C_{20}$ heterocycloalkyl; $A_1$ is $-C_2H_4-$; $A_3$ is $-CH_2-$, $-C_2H_4-$, $-C_3H_6-$, or deleted; $B_1$ is $-NH-$; $D_1$ is $-CH_2-$ or $-CH(CH_3)-$; $E_2$ is H; and $E_3$ is aryl, heteroaryl, $C_3$-$C_8$ cycloalkyl, $C_5$-$C_8$ cycloalkenyl, or $C_3$-$C_8$ heterocycloalkyl.

4. A pharmaceutical composition comprising a compound of the formula:

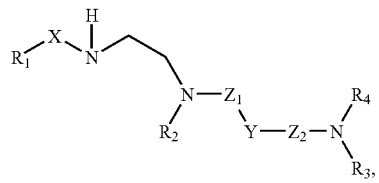

wherein

X is $-CH_2-$, $-C_2H_4-$, or $-C_3H_6-$;

Y is aryl, heteroaryl, $C_3$-$C_8$ cycloalkyl, $C_5$-$C_8$ cycloalkenyl, $C_3$-$C_8$ heterocycloalkyl, or $C_5$-$C_8$ heterocycloalkenyl;

each of $Z_1$ and $Z_2$, independently, is $-CH_2-$, $-C_2H_4-$, or $-C_3H_6-$;

$R_1$ is aryl or heteroaryl;

$R_2$ is $-A_1-B_1-D_1-E_1$;

$R_3$ is $-A_2-B_2-D_2-E_2$; and $R_4$ is $-A_3-B_3-D_3-E_3$ or, together with $R_3$, is $C_4-C_{20}$ heterocycloalkyl;

in which $A_1$ is $-CH_2-$, $-C_2H_4-$, $-C_3H_6-$, $-C_4H_8-$, or $-C_5H_{10}-$; is $-NR-$; $D_1$ is $-CH_2-$, $-C_2H_4-$, or $-C_3H_6-$; and $E_1$ is aryl, or heteroaryl; $A_2$ deleted; $B_2$ is deleted; $D_2$ is deleted; and $E_2$ is H, $C_3-C_8$ cycloalkyl, $C_5-C_8$ cycloalkenyl, $C_3-C_8$ heterocycloalkyl, $C_5-C_8$ heterocycloalkenyl, aryl, or heteroaryl; $A_3$ is $-CH_2-$, $-C_2H_4-$, $-C_3H_6-$, $-C_4H_8-$, $-C_5H_{10}-$, or deleted; $B_3$ is deleted; $D_3$ is deleted; and $E_3$ is $C_3C_8$ cycloalkyl, $C_5-C_8$ cycloalkenyl, $C_3-C_8$ heterocycloalkyl, $C_5-C_8$ heterocycloalkenyl, aryl, or heteroaryl; and a pharmaceutically acceptable carrier.

5. The composition of claim 4, wherein X is $-CH_2-$ or $-CH(CH_3)-$, Y is phenyl, $Z_1$ is $-CH_2-$, and $Z_2$ is $-CH_2-$.

6. The composition of claim 5, wherein $R_3$ is $-A_2-B_2-D_2-E_2$ or, together with $R_4$, is $C_4-C_{20}$ heterocycloalkyl; $A_1$ is $-C_2H_4-$ $A_3$ is $-CH_2-$, $-C_2H_4-$, $-C_3H_6-$, or deleted; $B_1$ is $-NH-$; $D_1$ is $-CH_2-$ or $-CH(CH_3)-$; $E_2$ is H; $E_3$ is aryl, heteroaryl, $C_3-C_8$ cycloalkyl, $C_5-C_8$ cycloalkenyl, or $C_3-C_8$ heterocycloalkyl.

\* \* \* \* \*